(12) United States Patent
Busalacchi et al.

(10) Patent No.: US 12,053,374 B2
(45) Date of Patent: *Aug. 6, 2024

(54) MEDICAL VALVE AND LEAFLET PROMOTING TISSUE INGROWTH

(71) Applicant: EDWARDS LIFESCIENCES CORPORATION, Irvine, CA (US)

(72) Inventors: Karl Busalacchi, Flagstaff, AZ (US); Benjamin D. Campbell, Flagstaff, AZ (US); Kyle W. Colavito, Flagstaff, AZ (US); Carl M. Conway, Flagstaff, AZ (US); Cody L. Hartman, Flagstaff, AZ (US); Roy Manygoats, Jr., Flagstaff, AZ (US); Frank E. Myers, Flagstaff, AZ (US); Vi T. Pham, Flagstaff, AZ (US); Joshua A. Sprinkle, Flagstaff, AZ (US); David M. Warlop, Flagstaff, AZ (US); Nathan L. Bennett, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/884,749

(22) Filed: Aug. 10, 2022

(65) Prior Publication Data
US 2022/0378575 A1  Dec. 1, 2022

Related U.S. Application Data

(63) Continuation of application No. 16/129,671, filed on Sep. 12, 2018, now Pat. No. 11,439,502.
(Continued)

(51) Int. Cl.
*A61F 2/24* (2006.01)
*A61F 2/00* (2006.01)
(Continued)

(52) U.S. Cl.
CPC .......... *A61F 2/2418* (2013.01); *A61F 2/0077* (2013.01); *A61F 2/2412* (2013.01);
(Continued)

(58) Field of Classification Search
CPC ........ A61F 2/24; A61F 2/2412; A61F 2/2418; A61F 2/2463; A61F 2/0077;
(Continued)

(56) References Cited

U.S. PATENT DOCUMENTS

| 654,799 A | 7/1900 | Levett |
|---|---|---|
| 3,739,402 A | 6/1973 | Kahn et al. |

(Continued)

FOREIGN PATENT DOCUMENTS

| AU | 2013363172 A1 | 7/2015 |
|---|---|---|
| AU | 2017202405 A1 | 4/2017 |

(Continued)

OTHER PUBLICATIONS

Clough, Norman E. Introducing a New Family of GORE ePTFE Fibers (2007), pp. 1-10.
(Continued)

*Primary Examiner* — Dinah Baria
(74) *Attorney, Agent, or Firm* — Yi Zhang; CHANG & HALE LLP

(57) ABSTRACT

Described embodiments are directed toward centrally-opening leaflet prosthetic valve devices having synthetic leaflets that are configured to promote and encourage tissue ingrowth thereon and/or therein. The leaflets are coupled to a leaflet frame to form a prosthetic valve suitable for use in biological anatomy.

14 Claims, 14 Drawing Sheets

Related U.S. Application Data

(60) Provisional application No. 62/579,760, filed on Oct. 31, 2017.

(51) Int. Cl.
*A61L 27/16* (2006.01)
*A61L 27/50* (2006.01)
*A61L 27/56* (2006.01)
*A61L 27/28* (2006.01)

(52) U.S. Cl.
CPC .......... *A61F 2/2415* (2013.01); *A61F 2/2427* (2013.01); *A61F 2/2463* (2013.01); *A61L 27/16* (2013.01); *A61L 27/507* (2013.01); *A61L 27/56* (2013.01); *A61F 2002/009* (2013.01); *A61F 2/24* (2013.01); *A61F 2/246* (2013.01); *A61F 2/2466* (2013.01); *A61F 2210/0014* (2013.01); *A61F 2210/0076* (2013.01); *A61F 2220/0016* (2013.01); *A61F 2220/005* (2013.01); *A61F 2220/0075* (2013.01); *A61F 2230/0069* (2013.01); *A61F 2240/001* (2013.01); *A61F 2250/0051* (2013.01); *A61F 2250/0069* (2013.01); *A61L 27/28* (2013.01)

(58) Field of Classification Search
CPC .. A61F 2250/0051; A61L 27/56; A61L 27/28; B32B 27/302; B32B 27/304; B32B 2535/00
See application file for complete search history.

(56) References Cited

U.S. PATENT DOCUMENTS

| | | |
|---|---|---|
| 3,953,566 A | 4/1976 | Gore |
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St. Germain et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Enker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |

(56) References Cited

U.S. PATENT DOCUMENTS

| | | |
|---|---|---|
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |

(56) References Cited

U.S. PATENT DOCUMENTS

| | | |
|---|---|---|
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |

(56) References Cited

U.S. PATENT DOCUMENTS

| | | |
|---|---|---|
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172081 A1* | 6/2014 | Bruchman ............ A61F 2/2415 156/185 |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1 | 9/2016 | Lim et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0257369 A1 | 8/2022 | Burkart et al. |
| 2022/0273426 A1 | 9/2022 | Hagaman et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |

(56) References Cited

FOREIGN PATENT DOCUMENTS

| | | |
|---|---|---|
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102724937 A | 10/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2489331 A2 | 8/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-000460 A | 1/2001 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-506439 A | 2/2013 |
| JP | 2013-543399 A | 12/2013 |
| JP | 2014-513585 A | 6/2014 |
| JP | 2014-517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A2 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |

(56) References Cited

FOREIGN PATENT DOCUMENTS

| | | |
|---|---|---|
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |
| WO | 2014/099150 A1 | 6/2014 |
| WO | 2014/099163 A1 | 6/2014 |
| WO | 2014/099722 A1 | 6/2014 |
| WO | 2014/144937 A2 | 9/2014 |
| WO | 2014/149319 A1 | 9/2014 |
| WO | 2014/181188 A2 | 11/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |
| WO | 2019/246268 A1 | 12/2019 |

OTHER PUBLICATIONS

English translation of RU2434604 (C1), filed Apr. 30, 2010, translation powered by EPO and Google, 8 pages.
Forward citations for E12 obtained from: https://scholar.google.com/scholar?cites=5981833429320176658&assdt=2005&sciodt=0,5&hl= en.
Google Image Search Results, "S-Shaped", accessed Nov. 1, 2013.
International Preliminary Report on Patentability received for PCT Patent Application No. PCT/US2018/050769, mailed on May 14, 2020, 8 pages.
Mano Thubrikar, "The Aortic Valve", Chapter 1: Geometry of the Aortic Valve, CRC Press, Inc., Informa Healthcare, 2011, 40 pages.
Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.

* cited by examiner

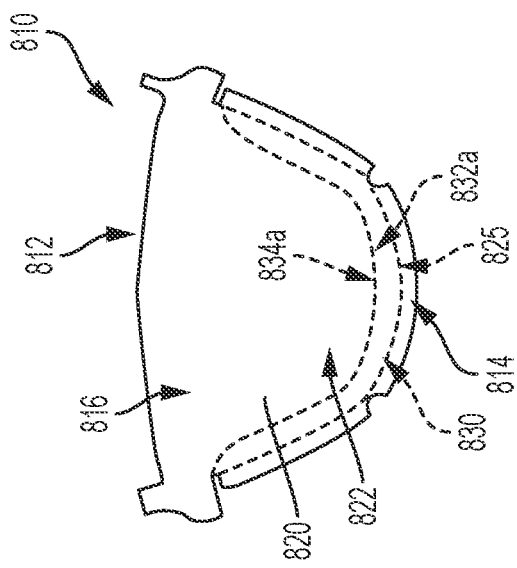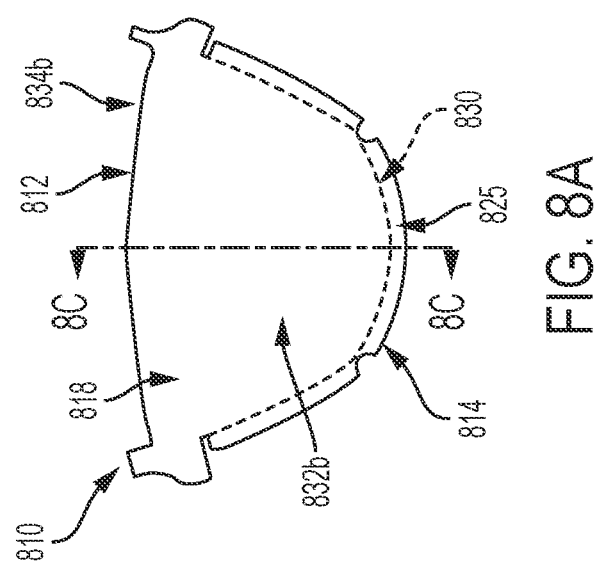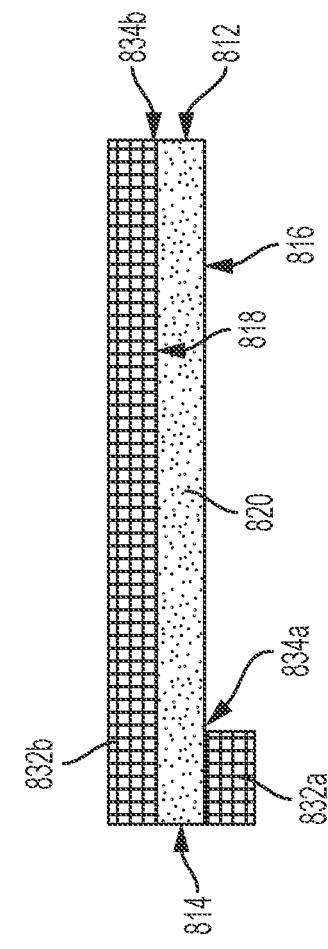

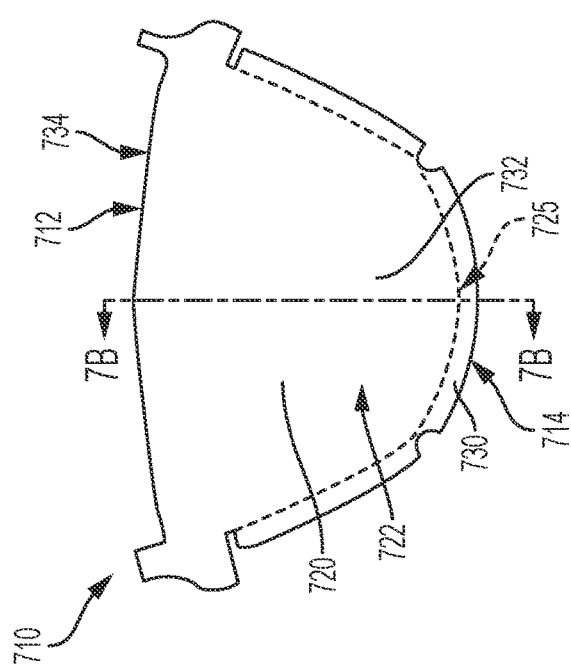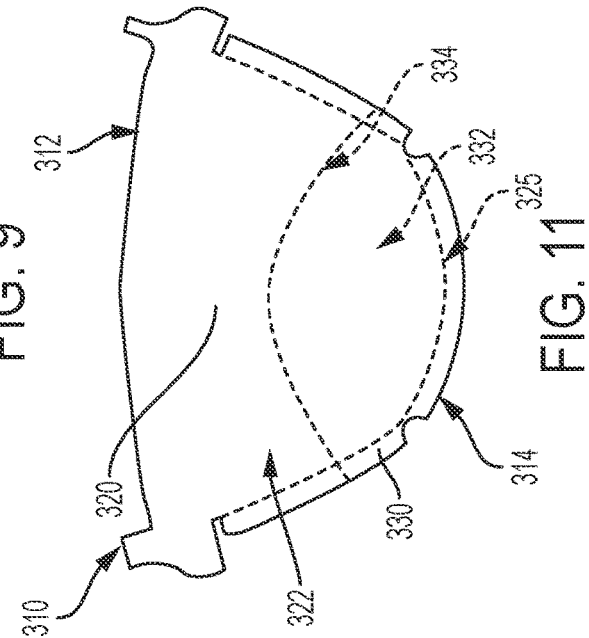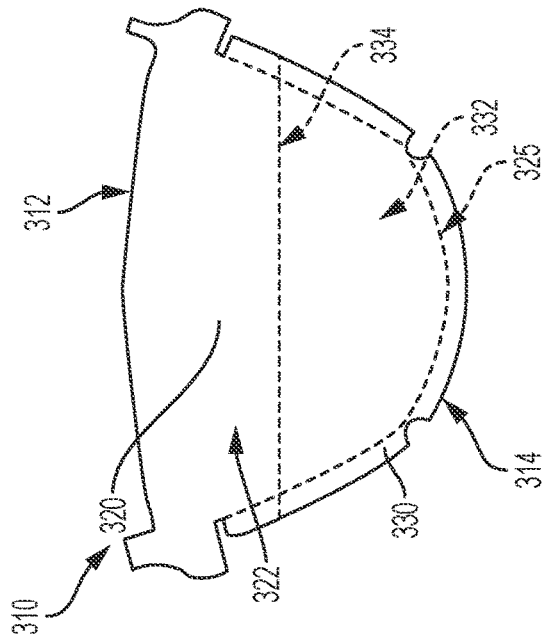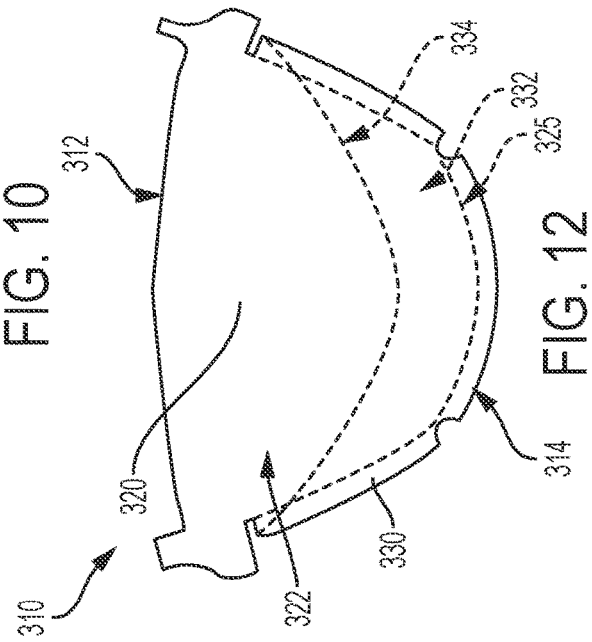
FIG. 9
FIG. 10
FIG. 11
FIG. 12

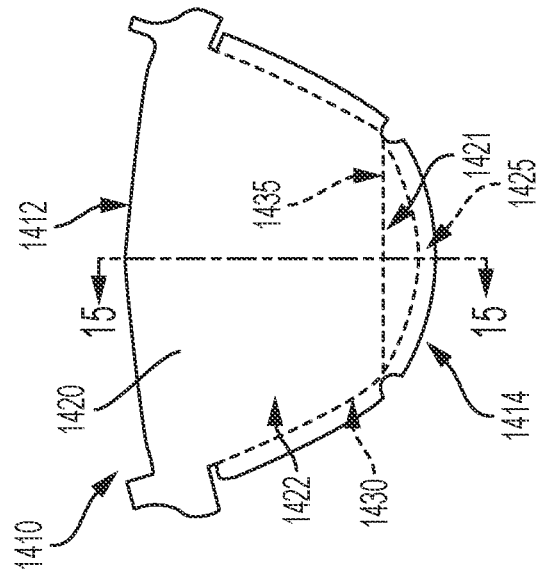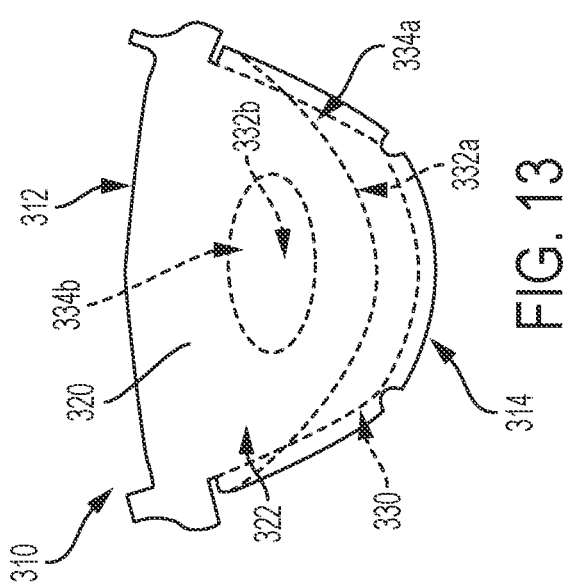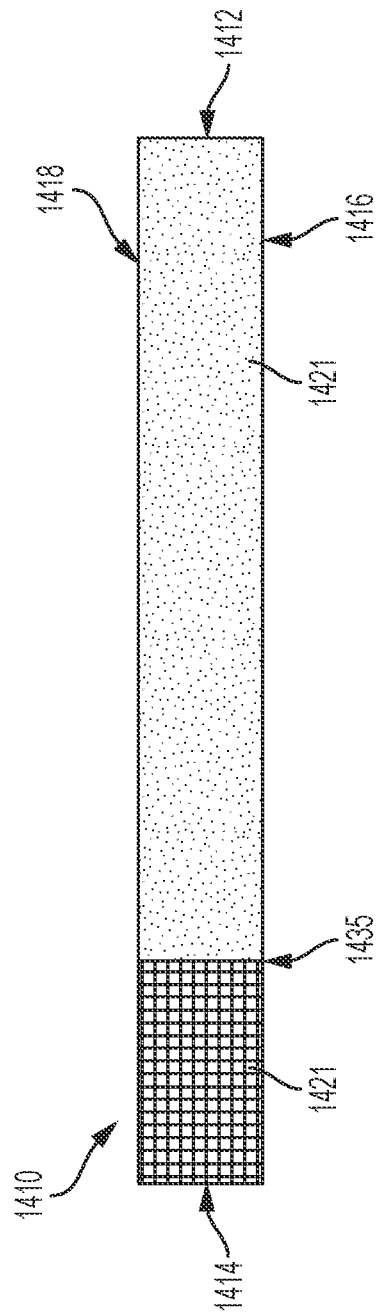

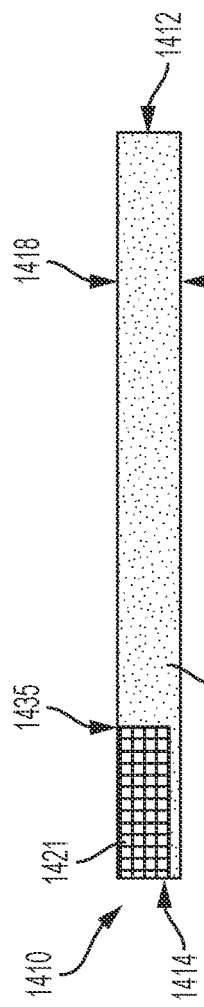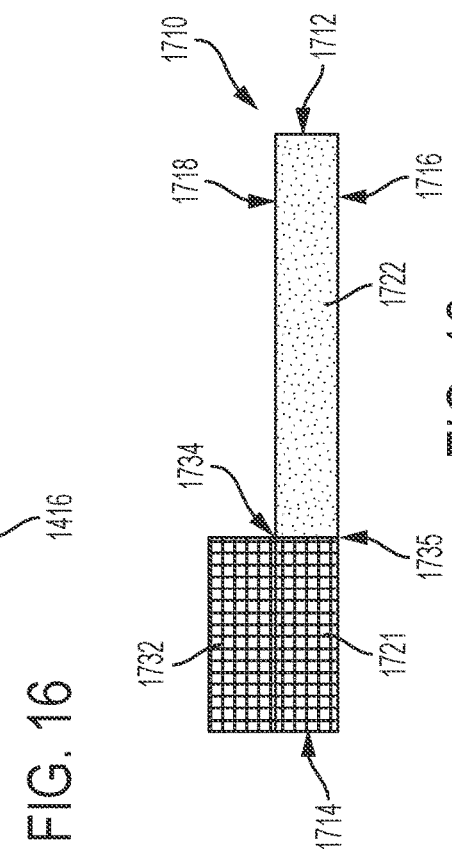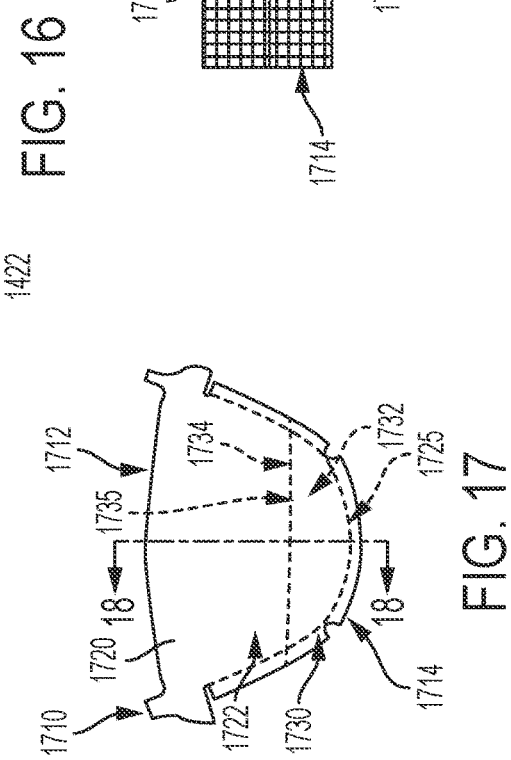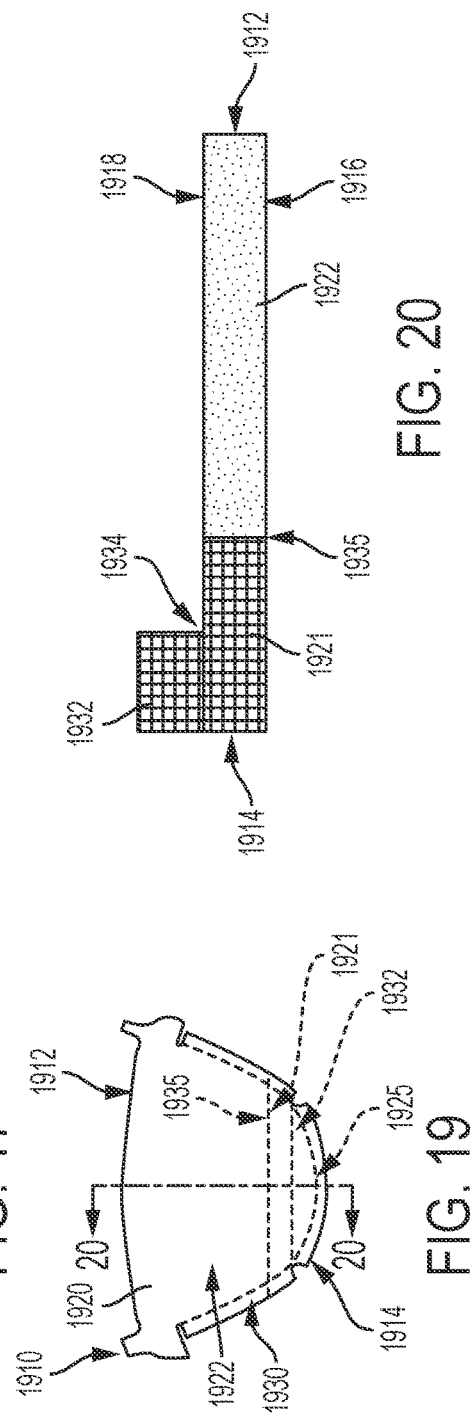

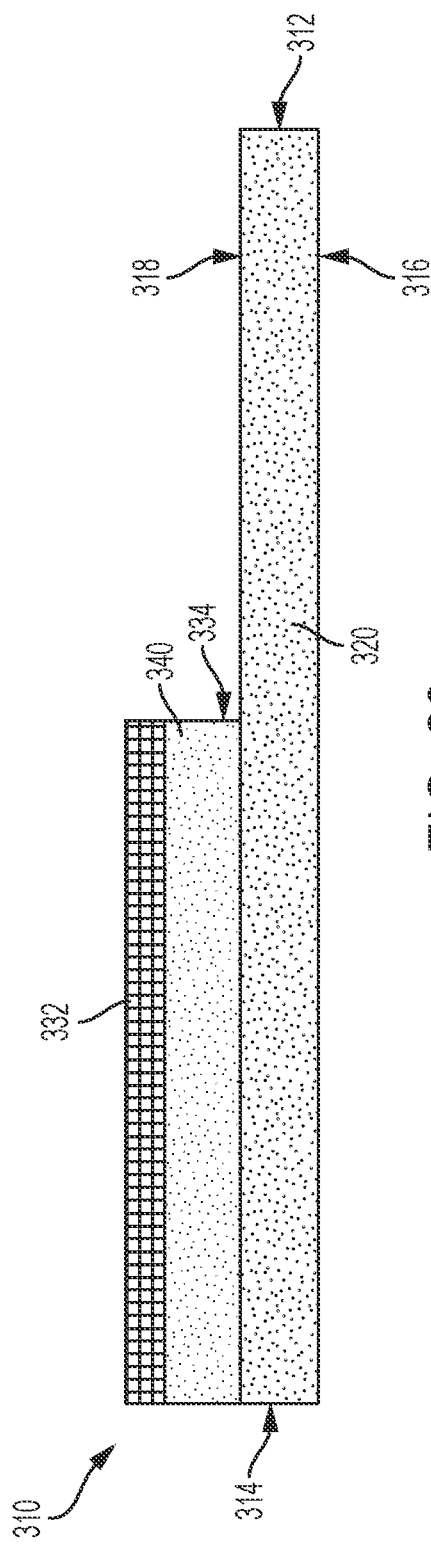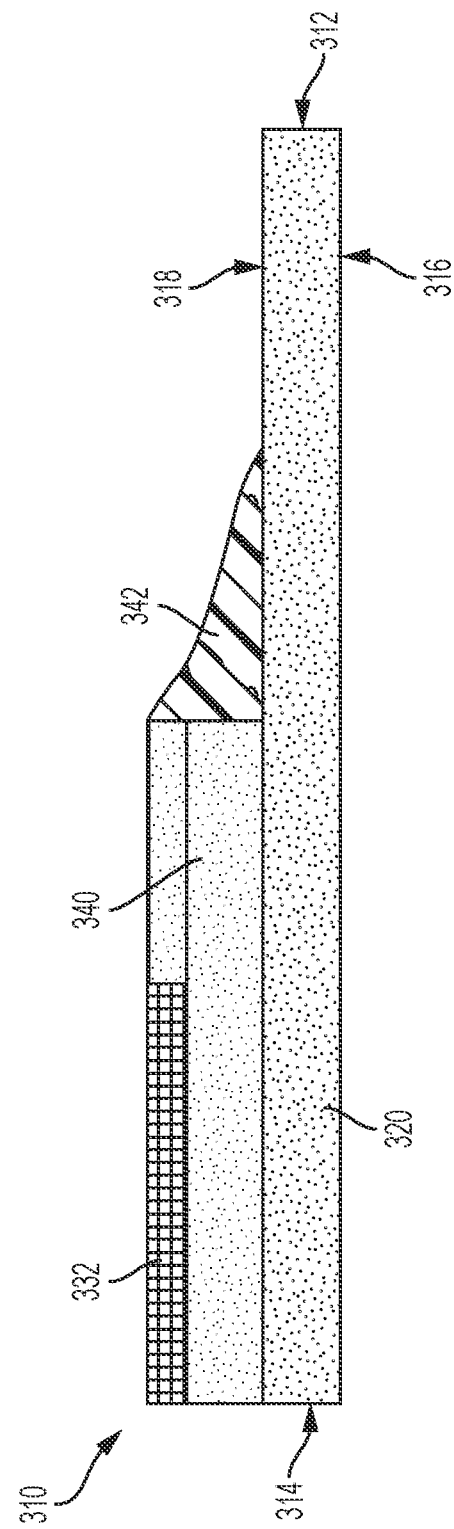

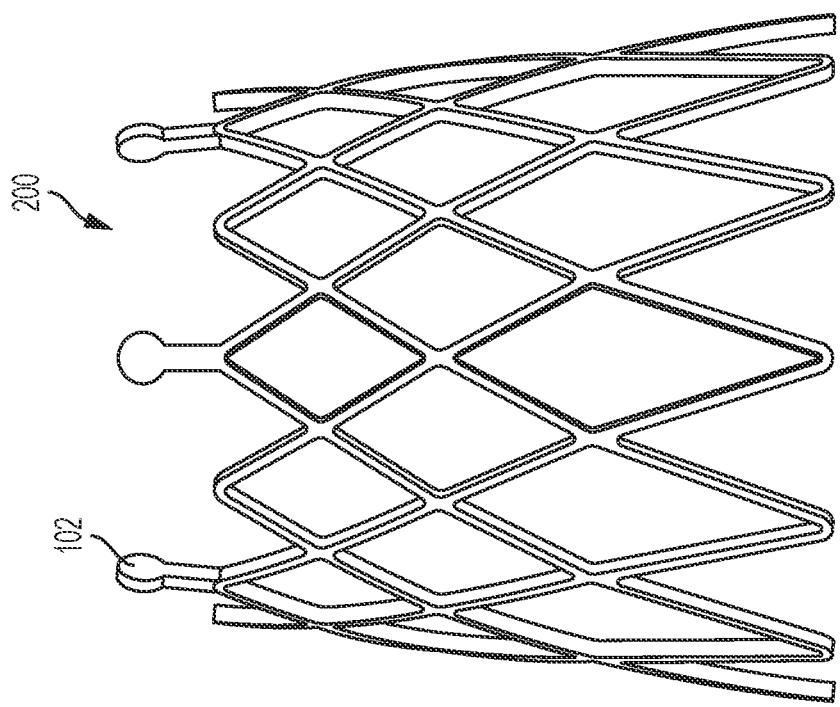
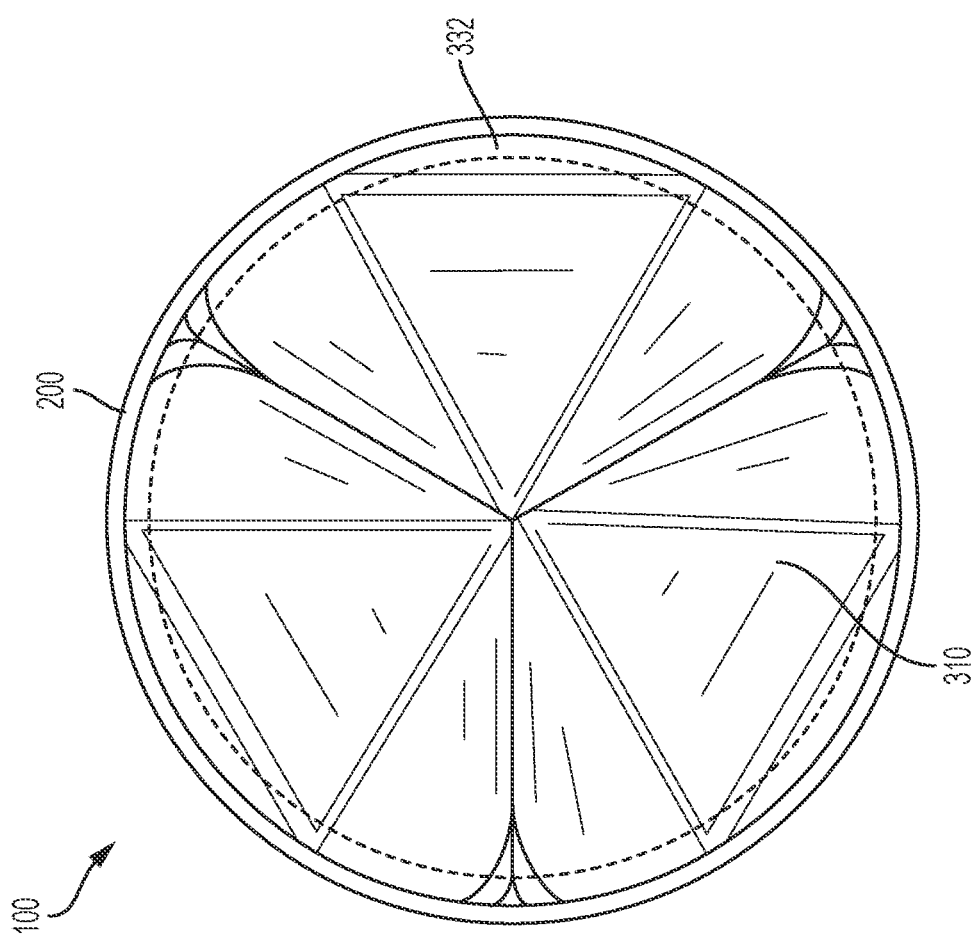

MEDICAL VALVE AND LEAFLET PROMOTING TISSUE INGROWTH

CROSS-REFERENCE TO RELATED APPLICATION

This application is a continuation of U.S. application Ser. No. 16/129,671, filed Sep. 12, 2018, which claims the benefit of Provisional Application No. 62/579,760, filed Oct. 31, 2017, which are incorporated herein by reference in their entireties for all purposes.

FIELD

The present disclosure relates generally to prosthetic valves and more specifically to flexible synthetic leaflets for use in prosthetic heart valve devices.

BACKGROUND

A number of fabrication techniques have been used to manufacture synthetic leaflets for use in prosthetic valves. In many cases, the resulting leaflet is supported on a prosthetic valve frame and defines a flap having a mounting edge where the leaflet is coupled to the prosthetic valve frame and a free edge that allows the flap to move. These prosthetic valve frames may include one, two, three, or more than three leaflets. The leaflet generally moves or transitions between open and closed configurations under the influence of fluid pressure in a patient's anatomy. In operation, the leaflets open when the fluid pressure on the inflow side of the prosthetic valve (e.g., upstream of the prosthetic valve) exceeds the fluid pressure on the outflow side of the prosthetic valve (e.g., downstream of the prosthetic valve) and closes when the fluid pressure on the outflow side of the prosthetic valve exceeds the fluid pressure on the inflow side of the prosthetic valve. The free edges of the leaflets coapt (either partially or completely) under the influence of downstream fluid pressure, which operates to minimize or prevent downstream blood from flowing retrograde through the prosthetic valve. Generally, the term "distal" is used in the disclosure to refer to the outflow end (distal end) or outflow direction of a prosthetic valve, and in turn the term "proximal" is used to refer to the inflow end of a prosthetic valve, or a direction opposite the direction of primary flow through the prosthetic valve.

The tissue response associated with the implantation of conventional prosthetic heart valves with synthetic leaflets can lead to a number of known complications, as well as decreased leaflet performance in some instances. It is believed that conventional leaflet designs that include materials that are impermeable or otherwise inhibitory to cellular tissue ingrowth perpetually traumatize endothelial cells surrounding the valve and/or leaflet, causing inflammation and promoting platelet activation. One potential result of this response by the body is thrombus formation, which can lead to a number of known complications.

SUMMARY

According to one example, ("Example 1"), a prosthetic valve includes a leaflet frame and a leaflet construct including a synthetic leaflet, wherein each leaflet includes a portion configured to promote tissue ingrowth thereon such that tissue is encouraged to grow between the leaflet frame and the leaflet.

According to another example, ("Example 2") further to Example 1, the leaflet includes a tissue ingrowth curtain coupled to an underlying leaflet base, wherein the tissue ingrowth curtain is configured to promote tissue ingrowth.

According to another example, ("Example 3") further to Example 2, the leaflet includes a plurality of tissue ingrowth curtains coupled to the underlying leaflet base, wherein each tissue ingrowth curtain of the plurality of tissue ingrowth curtains is configured to promote tissue ingrowth.

According to another example, ("Example 4") further to Example 3, the plurality of ingrowth curtains includes a first tissue ingrowth curtain and a second tissue ingrowth curtain, wherein the first tissue ingrowth curtain is coupled to a first side of the underlying leaflet base of the leaflet, and wherein the second tissue ingrowth curtain is coupled to a second side of the underlying leaflet base of the leaflet.

According to another example, ("Example 5") further to Examples 2 to 4, the tissue ingrowth curtain comprises a porous membrane.

According to another example, ("Example 6") further to Example 5, the tissue ingrowth curtain comprises a fluoropolymer membrane.

According to another example, ("Example 7") further to Example 6, the fluoropolymer membrane includes an expanded fluoropolymer.

According to another example, ("Example 8") further to Example 7, the expanded fluoropolymer membrane comprises ePTFE.

According to another example, ("Example 9") further to Examples 2 to 8, the tissue ingrowth curtain is bonded to the underlying leaflet base.

According to another example, ("Example 10") further to any of the preceding Examples, the leaflet frame is configured to promote tissue ingrowth.

According to another example, ("Example 11") further to any of the preceding Examples, tissue is encouraged to grow across the leaflet frame onto the leaflet.

According to another example, ("Example 12") further to any of the preceding Examples, the leaflet frame is covered with a tissue ingrowth promoting material.

According to another example, ("Example 13") further to Example 11, the tissue ingrowth promoting material is a fabric.

According to another example, ("Example 14") further to Examples 2 to 13, the tissue ingrowth curtain is coupled to the underlying leaflet base with an adhesive.

According to another example, ("Example 15") further to any of the preceding Examples, the leaflet includes a porous membrane having a first zone and a second zone, wherein a first elastomeric material is contained within the first zone of the porous membrane of the leaflet, and wherein the second zone of the porous membrane of the leaflet is free of the first elastomeric material.

According to another example, ("Example 16") further to Example 15, the tissue ingrowth curtain is coupled to the second zone of the porous membrane of the leaflet.

According to another example, ("Example 17") further to Example 16, the tissue ingrowth curtain is coupled to the second zone of the porous membrane of the leaflet with an adhesive.

According to another example, ("Example 18") further to Examples 15 to 17, the porous membrane of the leaflet includes a first side and a second side and wherein the tissue ingrowth curtain completely covers the second zone of the porous membrane of the leaflet on the first side of the porous membrane of the leaflet.

According to another example, ("Example 19") further to Examples 15 to 18, the porous membrane is a fluoropolymer membrane.

According to another example, ("Example 20") further to Example 19, the fluoropolymer membrane includes an expanded fluoropolymer.

According to another example, ("Example 21") further to Example 20, the expanded fluoropolymer comprises ePTFE.

According to another example, ("Example 22") further to Examples 15 to 21, the first elastomeric material is silicone.

According to another example, ("Example 23") further to Examples 15 to 21, the first elastomeric material is a fluoroelastomer.

According to another example, ("Example 24") further to Examples 15 to 21, wherein the first elastomer is a urethane.

According to another example, ("Example 25") further to Examples 15 to 21, the first elastomeric material is a TFE/PMVE copolymer.

According to another example, ("Example 26") further to Examples 15 to 25, a second elastomeric material is contained within the first zone of the porous membrane of the leaflet.

According to another example, ("Example 27") further to any of the preceding Examples, the tissue ingrowth curtain is coupled to the underlying leaflet base with an adhesive such that the adhesive forms a transition between one or more edges of the tissue ingrowth curtain and the underlying leaflet base.

According to another example, ("Example 87") further to Example 27, a fillet is formed across a transition between the tissue ingrowth curtain and the leaflet base.

According to another example, ("Example 29") a method of forming a synthetic leaflet includes providing a first synthetic porous membrane, imbibing one or more portions of the first porous membrane with one or more filler materials such that one or more of the imbibed portions or areas are rendered unsuitable for supporting or promoting tissue ingrowth. The method further includes providing a second synthetic porous membrane that is suitable for promoting tissue ingrowth thereon, and securing the second porous membrane to the first porous membrane.

According to another example, ("Example 30") a method of forming a synthetic leaflet includes providing a synthetic porous membrane, wherein the porous membrane includes a first zone and a second zone, the first and second zones being suitable for promoting tissue ingrowth thereon. The method further includes imbibing a first zone of the porous membrane with a filler material such that imbibed first portion of the porous membrane is rendered unsuitable for supporting or promoting tissue ingrowth thereon.

According to one example ("Example 31"), a method of treating a failing or dysfunctional native valve with a prosthetic valve, the method comprising: replacing the native valve with a prosthetic valve in accordance with any of Examples 1 to 28.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 8A is a top view of a leaflet, according to some embodiments;

FIG. 8B is a top view of a leaflet, according to some embodiments;

FIG. 8C is a cross section view of the leaflet shown in FIG. 8A taken along line 8C-8C, according to some embodiments;

FIG. 9 is a top view of a leaflet, according to some embodiments;

FIG. 10 is a top view of a leaflet, according to some embodiments;

FIG. 11 is a top view of a leaflet, according to some embodiments;

FIG. 12 is a top view of a leaflet, according to some embodiments;

FIG. 13 is a top view of a leaflet, according to some embodiments;

FIG. 14 is a top view of a leaflet, according to some embodiments;

FIG. 15 is a cross section view of the leaflet shown in FIG. 14 taken along line 15-15, according to some embodiments;

FIG. 16 is a cross section view of a leaflet, according to some embodiments;

FIG. 17 is a top view of a leaflet, according to some embodiments;

FIG. 18 is a cross section view of the leaflet shown in FIG. 17 taken along line 18-18, according to some embodiments FIG. 19 is a top view of a leaflet, according to some embodiments;

FIG. 20 is a cross section view of the leaflet shown in FIG. 19 taken along line 20-20, according to some embodiments

FIG. 23 is a cross section view of a leaflet, according to some embodiments;

FIG. 24 is a cross section view of a leaflet, according to some embodiments;

FIG. 28A is a top view of an outflow side of another prosthetic valve, according to some embodiments; and FIG. 28B is a side view of a frame of the prosthetic valve shown in FIG. 28A;

DETAILED DESCRIPTION

Figure 1A:
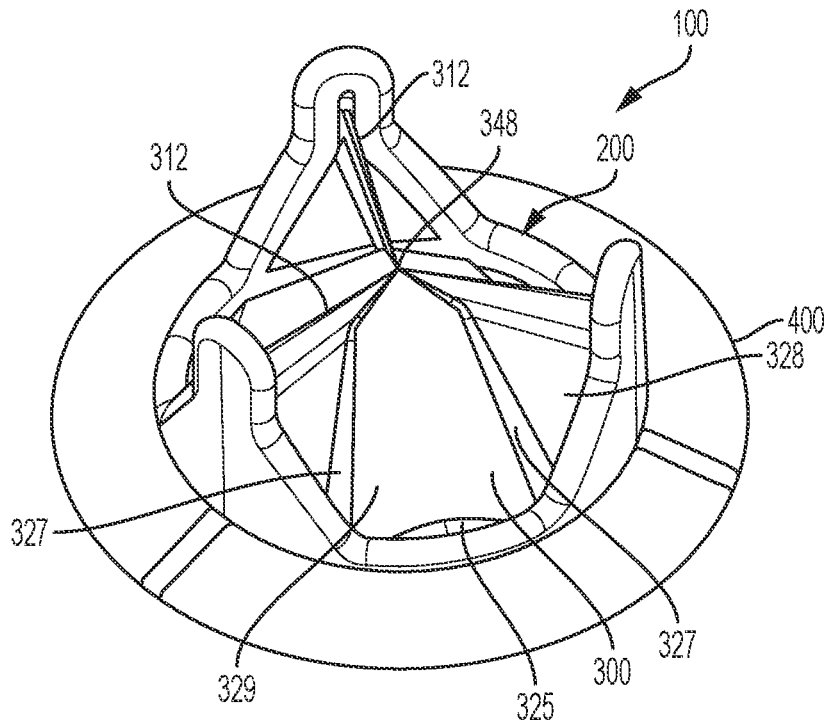
FIG. 1A is an outflow side isometric view of a prosthetic heart valve in accordance with an embodiment.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a flexible component of a one-way valve wherein the leaflet is operable to move between an open and closed position under the influence of a pressure differential. In an open position, the leaflet allows blood to flow through the valve. In a closed position, so as to block or occlude the valve orifice and partially or entirely prevent flow in response to differential fluid pressure. It will be appreciated that, in some instances, coaptation of adjacent leaflets may operate to completely block the flow of fluid (e.g., blood) through the prosthetic valve, while in others coaptation of adjacent leaflets may operate to block less than all of the flow of fluid (e.g., blood) through the prosthetic valve.

In embodiments comprising multiple leaflets, each leaflet generally cooperates with at least one neighboring or adjacently situated leaflet to block or restrict the retrograde flow of blood. The pressure differential in the blood is caused, for example, by the contraction of a ventricle or atrium of the heart, such pressure differential typically resulting from a fluid pressure building up on one side of the leaflets when closed. As the pressure on the inflow side of the valve rises above the pressure on the outflow side of the valve, the leaflets open and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The embodiments and examples discussed herein include various apparatus, systems, and methods for a prosthetic valve, such as, but not limited to, cardiac valve replacement. In some examples, the prosthetic valve is operable as a one-way valve wherein the prosthetic valve defines a valve orifice into which leaflets open to permit flow and close so as to occlude the valve orifice and prevent flow in response to differential fluid pressure. In the instant disclosure, the examples are primarily described in association with prosthetic valves or mechanisms of similar structure and/or function, including surgically implanted valves, although it should be readily appreciated features of such examples are equally applicable to transcatheter cardiac valve applications.

Figure 1B:
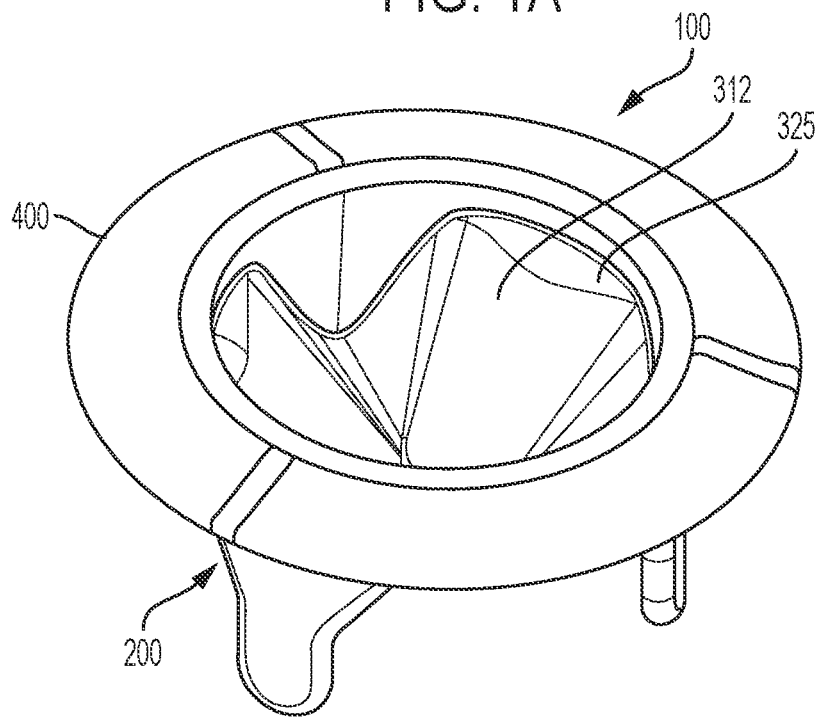
FIG. 1B is an inflow side isometric view of the embodiment of the valve of FIG. 1A.

FIGS. 1A and 1B are outflow and inflow, respectfully, views of a prosthetic valve 100 in the form of a prosthetic heart valve, in accordance with an embodiment. The components of the prosthetic valve 100 shown in FIGS. 1A and 1B include a leaflet frame 200 and a plurality of leaflets 310 coupled to the leaflet frame 200. In some examples, the prosthetic valve 100 includes a sewing cuff 400.

The leaflet frame 200 is operable to hold and support the leaflets 310. Examples of suitable leaflet frame constructions and sewing cuffs are illustrated and described in U.S. patent application Ser. Nos. 13/833,650, 14/973,589, and 14/853,654, the contents of each of which are incorporated herein by reference. It will be appreciated that the leaflet frame 200 can be etched, cut, laser cut, stamped, or three-dimensional printed, among other suitable processes, into an annular structure or a sheet of material, with the sheet then formed into an annular structure. In various examples, the leaflet frame 200 can comprise, such as, but not limited to, any biocompatible and elastically deformable metallic or polymeric material including a shape-memory material, such as nitinol, a nickel-titanium alloy. Other materials suitable for the leaflet frame 200 include, but are not limited to, other titanium alloys, stainless steel, cobalt-nickel alloy, polypropylene, polyethylene terephthalate, PEEK, acetyl homopolymer, acetyl copolymer, other alloys, polymers, and thermoplastics, or any other material that is generally biocompatible having adequate physical and mechanical properties to function as a leaflet frame 200 as described herein.

In various embodiments, one or more portions of the leaflet frame 200 may be covered with material suitable for promoting tissue ingrowth. For example, the leaflet frame 200 can be wrapped with a material, suitable for promoting tissue ingrowth. In various examples, such tissue ingrowth promoting materials can be applied to leaflet frame 200 entirely, or alternatively to less than all of the leaflet frame 200. For example, suitable materials for promoting tissue ingrowth could be coupled to the leaflet frame inner surface and the leaflet frame outer surface of the leaflet frame and optionally between the leaflet frame projections prior to leaflet attachment. Some nonlimiting examples of materials that can be applied to the leaflet frame 200 (or other portions of the prosthetic valve 100) include expanded polytetrafluoroethylene (ePTFE), such as an ePTFE membrane, fabric, film, or coating, and a polyethylene terephthalate fabric (e.g., Dacron fabric).

Figure 2:
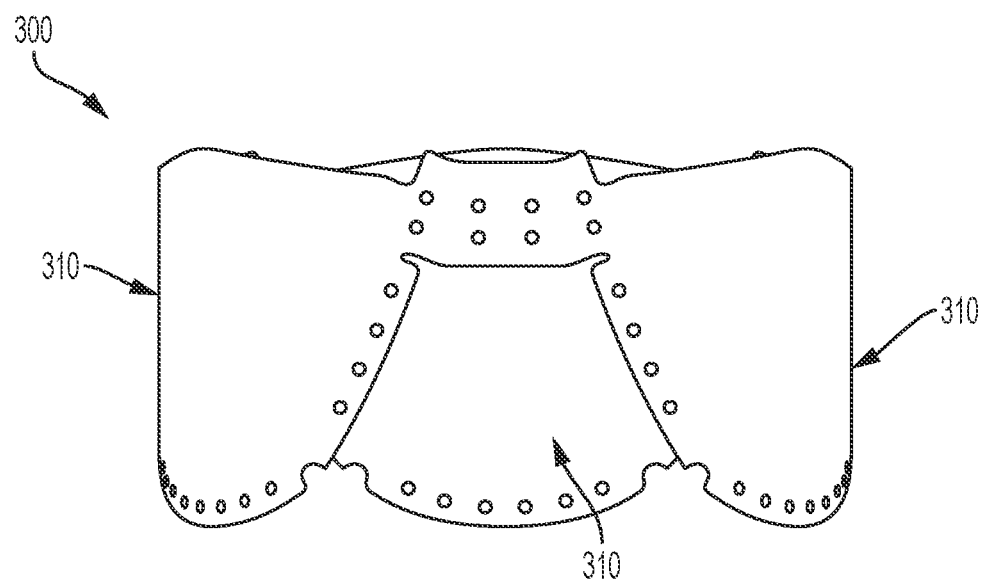
FIG. 2 is a front view of a leaflet construct, according to some embodiments.
Figure 3:
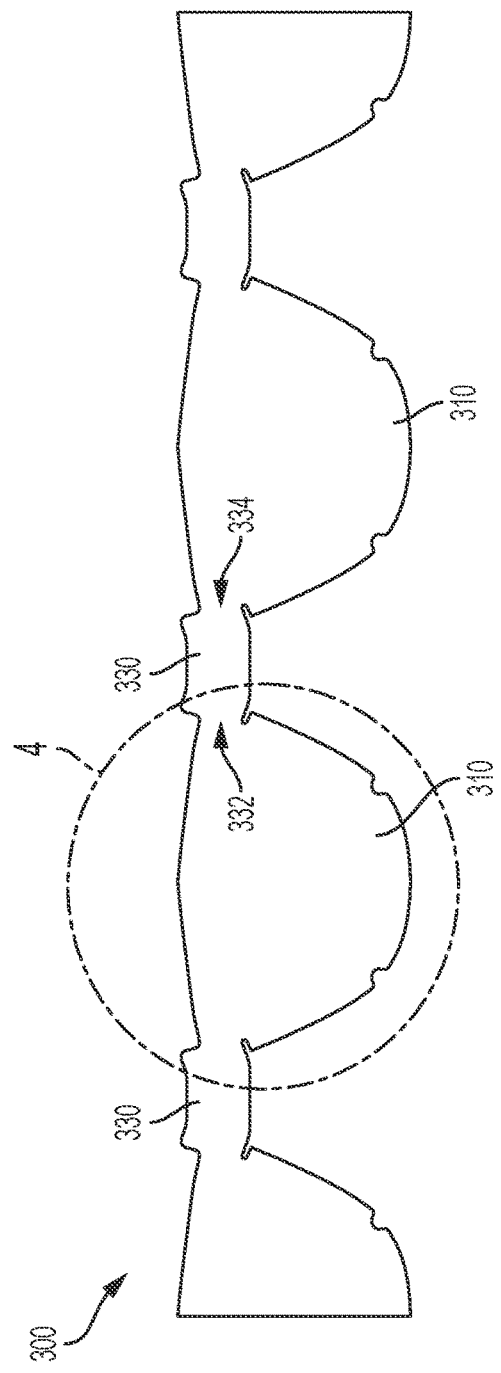
FIG. 3 is a representation of the leaflet frame shown in FIG. 2 that has been unrolled to a flat orientation, according to some embodiments.

The leaflets 310 are coupled to the leaflet frame 200 such that they each generally extend radially inwardly from the leaflet frame 200 toward a triple point 348, as shown in FIG. 1A. FIGS. 2 to 3 show a leaflet 310, according to some embodiments. FIG. 2 is a front view of a leaflet construct 300 including a plurality of leaflets 310. FIG. 3 is a representation of the leaflet construct 300 shown in FIG. 2 that has been longitudinally cut, opened, and laid flat to better illustrate the features of the leaflets 310. It should be appreciated that the location and illustration of the cut made through the leaflet in FIG. 3 is for illustration purposes only and should not be construed as limiting. It should also be appreciated that while the embodiments and examples discussed herein include prosthetic valves that includes multiple leaflets, and leaflet constructs that are comprised of multiple leaflets, the tissue ingrowth curtains and imbibing techniques discussed herein may be applied to synthetic leaflets for prosthetic valves incorporating one, two, three, or more than three leaflets.

Figure 5:
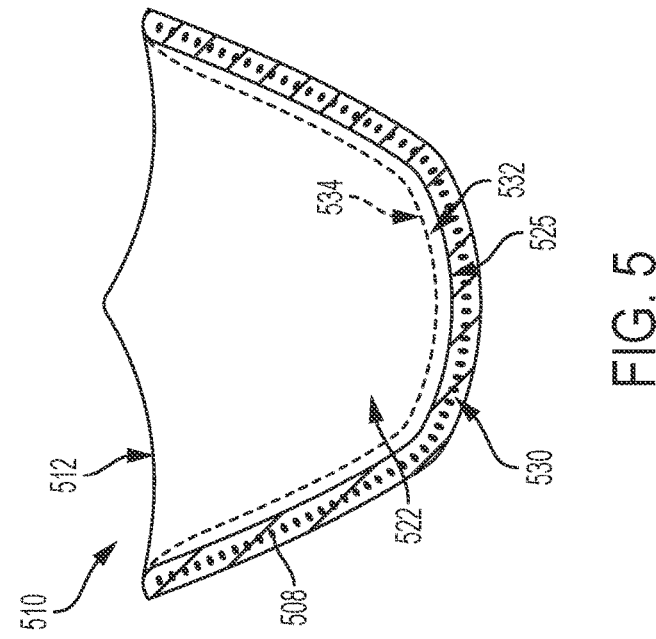
FIG. 5 is a representation of a leaflet, according to some embodiments.
Figure 4:
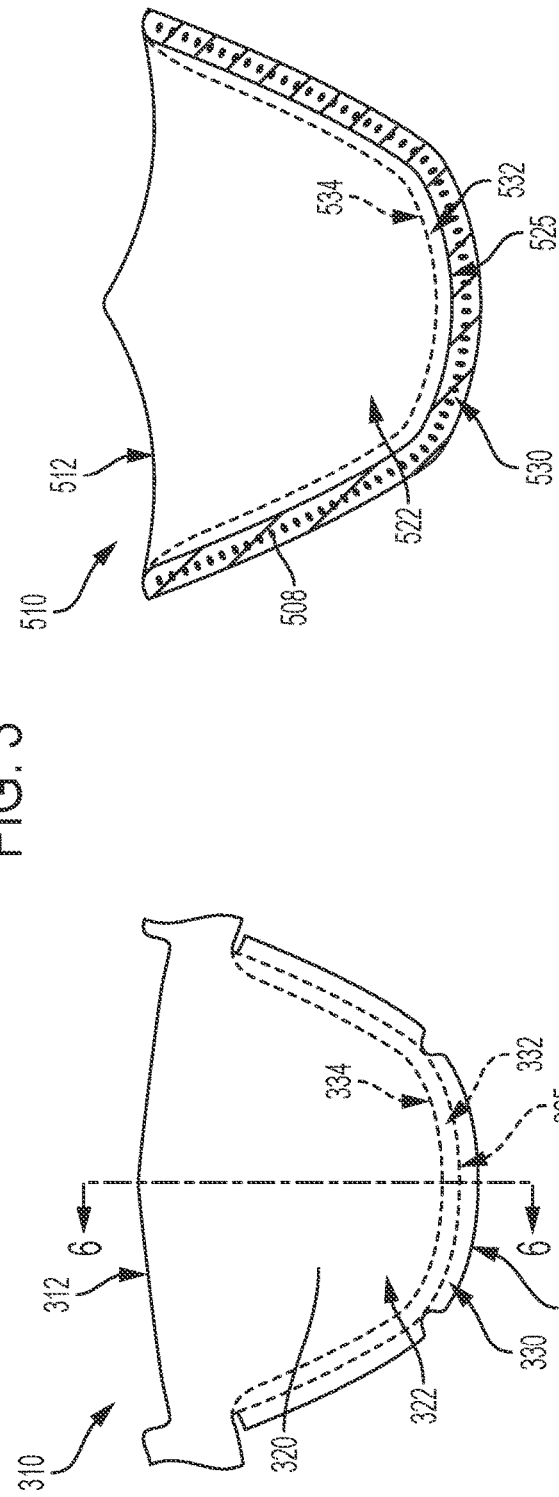
FIG. 4 is a magnified view of circle 4 in FIG. 3.

FIGS. 3 to 5 show several nonlimiting exemplary leaflet configurations. FIG. 4 is a magnified top view of the circle of FIG. 3, and shows one of the leaflets 310 of the leaflet construct 300 of FIG. 3. FIG. 5 is a top view of an alternative leaflet 510 for a prosthetic valve configuration wherein each leaflet 510 of the prosthetic valve forms an independent monolithic component that is coupled to a leaflet frame of a prosthetic valve independent of any other leaflets of the prosthetic. In a flat configuration, both leaflets 310 and 510 are generally configured in a shape of an isosceles trapezoid with bowed sides, as shown. It will be appreciated, however, that the leaflets adopt a different shape when applied to a leaflet frame of a prosthetic valve (see, e.g., FIGS. 1A and 1B). For example, a shape adopted by a leaflet when coupled to a leaflet frame is determined, at least in part, by a shape of the leaflet frame, a shape of the portion of the leaflet attached to the leaflet frame, and a fluid pressure that the leaflet encounters during operation, among other factors. In some examples, a shape of a leaflet may be influenced or altered by other techniques, such as, but not limited to, leaflet molding and shape-setting.

With specific reference now to FIG. 4, each of the leaflets 310 generally includes a leaflet attachment region 330, a leaflet belly region 322, and a leaflet free edge 312. In some examples, the leaflet belly region 322 terminates at the leaflet free edge 312. In some examples, the leaflet belly region 322 additionally or alternatively terminates at the leaflet attachment region 330. In some examples, a leaflet base 325 is defined at an intersection between the leaflet attachment region 330 and the leaflet belly region 322. In various examples, the leaflet belly region 322 of the leaflet 310 is the operating portion of the leaflet 310 when assembled into a prosthetic valve 100. In various examples, the leaflet attachment region 330 corresponds to the portion of the leaflet 310 configured for attachment to the leaflet frame 200. In some examples, the leaflet attachment region 330 extends around a portion of a periphery of the leaflet 310 and terminates into the leaflet free edge 312 on an opposing side of a center point of the leaflet free edge. In various examples, the leaflet attachment region 330 borders the leaflet belly region 322. In some examples, the leaflet 310 can be configured to wrap around one or more portions of the leaflet frame 200. Some examples of suitable methods for attaching the leaflet 310 to the leaflet frame 200 are illustrated and described in U.S. patent application Ser. Nos. 13/833,650, 14/973,589, and 14/853,654, mentioned above.

The leaflet 510 shown in FIG. 5 similarly includes a leaflet attachment region 530, a leaflet belly region 522, a leaflet free edge 512, and a leaflet base 525 defined at an intersection between the leaflet attachment region 530 and the leaflet belly region 522. As shown in FIG. 5, the leaflet 510 includes a tissue ingrowth curtain 532 that extends into the leaflet belly region 522 such that a boundary 534 is defined at an intersection of the tissue ingrowth curtain 532 and the leaflet belly region 522. Additionally, as shown, the leaflet 510 includes one or more features for securing the leaflet 510 to a corresponding leaflet frame. Though illustrated in FIG. 5 as a leaflet aperture 508, it will be appreciated that these features for securing the leaflet 510 to a corresponding leaflet frame may take any alternative suitable form without departing from the spirit or scope of the present disclosure. It will also be appreciated that, while not illustrated with such, the leaflet 510 may include similar features (e.g., leaflet apertures) for securing the leaflet 510 to the corresponding leaflet frame 200.

In accordance with various embodiments, the various leaflet constructs discussed herein including the leaflets are synthetic in that the leaflets and the various other portions of the leaflet constructs comprise one or more biocompatible materials that are not of a biological source and that are sufficiently compliant and strong for the particular purpose, such as a biocompatible polymer. In some embodiments, the leaflets comprise a membrane that is combined with an elastomeric material, such as a fluoroelastomer, to form a composite material, as disclosed herein. It will be appreciated that while various examples are discussed with regard to leaflet constructs 300 and 900, the various examples and embodiments discussed herein may be universally applied across each of the leaflet constructs and/or the various components of the leaflet constructs discussed herein.

In some examples, the leaflet construct 300 including leaflets 310 can be made by starting from a cylinder of polymer material that has been cut into a shape like that shown in FIGS. 2 and 3. In some other examples, a plurality of leaflets 310 are made from a sheet of polymer material that has been cut into a shape like that shown in FIG. 4 and subsequently coupled together into an annular shape like that shown in FIGS. 2 and 3. In some other examples, the leaflet construct 300 and/or the leaflets 310 may be formed by way of one or more compression or injection molding processes.

As mentioned above, the leaflets 310 are generally formed as a synthetic composite material. In various embodiments, the leaflets 310 include an underlying synthetic leaflet base material combined with a tissue ingrowth curtain that may be incorporated into the leaflet base material and/or coupled with the leaflet base material as explained further below. In some examples, the composite material forming the underlying synthetic leaflet base includes an expanded fluoropolymer membrane, which comprises a plurality of spaces within a matrix of fibrils, and an elastomeric material such as a fluoroelastomer imbibed or otherwise incorporated into the expanded fluoropolymer membrane. In some examples, the underlying leaflet base includes an imbibed porous monolayer. It will be appreciated that multiple types of fluoropolymer membranes and multiple types of elastomeric materials (and non-elastomeric materials) can be combined to form a composite material of the underlying leaflet base while remaining within the spirit and scope of the present disclosure. It should also be appreciated that the elastomeric material can include multiple elastomers, multiple types of non-elastomeric components, such as inorganic fillers, therapeutic agents, radiopaque markers, and the like while remaining within the spirit and scope of the present disclosure.

Further examples include a leaflet construct 300 comprising at least one fluoropolymer membrane layer, wherein the leaflet construct 300 comprises a composite having more than one fluoropolymer membrane layer, and wherein the at least one fluoropolymer membrane layer is an expanded fluoropolymer membrane layer. In some examples, the leaflet construct 300 comprises a composite material having at least one fluoropolymer membrane layer having a plurality of pores and an elastomer and/or an elastomeric material present in the pores of at least one of the fluoropolymer membrane layers.

In various examples, any of the leaflet constructs described herein (e.g., leaflet construct) may be formed of a biocompatible, synthetic material (e.g., including ePTFE and ePTFE composites, or other materials as desired). Other biocompatible polymers which can be suitable for use in synthetic leaflets include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet construct comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet construct further comprises a layer of an elastomer and/or an elastomeric material and/or a non-elastomeric material on the composite material. In accordance with some examples, the composite material comprises porous synthetic polymer membrane by weight in a range of about 10% to 90%.

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkyl-vinylethers (PAVE), urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluoromethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet construct is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet construct 300 further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

In accordance with an embodiment, the composite material can include an expanded fluoropolymer material made from porous ePTFE membrane, for instance as generally described in U.S. Pat. No. 7,306,729 to Bacino.

The expanded fluoropolymer membrane, used to form some of the composites described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

In various embodiments, the leaflet 310 is constructed in a manner that promotes tissue ingrowth. In some embodiments, the leaflet 310 may be constructed to encourage tissue ingrowth and proliferation across one or more discrete regions, portions, or sections of one or more of the materials forming the leaflet 310, or alternatively across an entirety of one or more of the materials forming the leaflet 310. Tissue ingrowth and proliferation may be promoted on an outflow side or surface of the leaflet 310, and/or on an inflow side or surface of the leaflet 310, and/or within one or more materials forming the leaflet.

According to some examples, as will be discussed in greater detail below, this promotion of tissue ingrowth is facilitated by the coupling of one or more synthetic tissue ingrowth curtains to one or more underlying leaflet base materials such that tissue is encouraged to grow (or is not otherwise prevented or inhibited from growing) into and/or onto the one or more tissue ingrowth curtains. That is, in some examples, one or more layers configured to promote tissue ingrowth may be applied to an underlying leaflet structure or material. In some examples, as described herein, the underlying leaflet structure or material may be configured to inhibit or prevent tissue ingrowth.

Additionally or alternatively, in some examples, this promotion of tissue ingrowth is facilitated by selectively imbibing, such as with one or more fluoroelastomers, one or more portions of the one or more materials forming the leaflet 310. That is, in some examples, in addition to or as an alternative to coupling one or more synthetic tissue ingrowth curtains to one or more underlying leaflet base materials, the underlying leaflet base materials themselves are configured to promote or accommodate tissue ingrowth. In some such examples, as discussed in greater detail below, underlying leaflet base materials are configured such that tissue is encouraged to grow (or is not otherwise prevented or inhibited from growing) into and/or onto one or more discrete or designated sections, portions, or regions of the one or more underlying leaflet base materials.

In various embodiments, the tissue ingrowth curtain generally includes an expanded fluoropolymer membrane, which comprises a plurality of spaces within a matrix of fibrils, and that is suitable for promoting and supporting the ingrowth of tissue. Other nonlimiting example materials include other biocompatible porous materials such as knit PTFE. However, as mentioned above, and as discussed in greater detail below, in some examples the tissue ingrowth curtain(s) may be applied to the underlying leaflet base in the form of one or more coatings.

In some examples, the tissue ingrowth curtain includes an expanded fluoropolymer material made from a porous ePTFE membrane. However, it will be appreciated that the tissue ingrowth curtain may be formed from a number of different types of membranes, including other fluoropolymer membranes, and other biocompatible porous materials such as knit PTFE. For instance, the expandable fluoropolymer can comprise PTFE homopolymer. In some examples, the tissue ingrowth curtain can be formed from copolymers of hexafluoropropylene and tetrafluoroethylene, such as Fluorinated Ethylene Propylene (FEP). In some examples, blends of PTFE, expandable modified PTFE and/or expanded copolymers of PTFE can be used. It will thus be appreciated that the tissue ingrowth curtain may be formed from a variety of different polymeric materials, provided they are biocompatible and possess or are modified to include a suitable microstructure suitable for promoting or supporting tissue ingrowth. In various examples, the tissue ingrowth curtains may range in thickness from between one microns and four hundred microns depending on the selected material.

In some examples, the polymeric material may include one or more naturally occurring and/or one or more artificially created pores, reliefs, or channels for supporting tissue ingrowth. Other biocompatible porous materials which can be suitable for use forming the tissue ingrowth curtain include but are not limited to the groups of urethanes, fluoropolymers, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing, for example.

Figure 6:
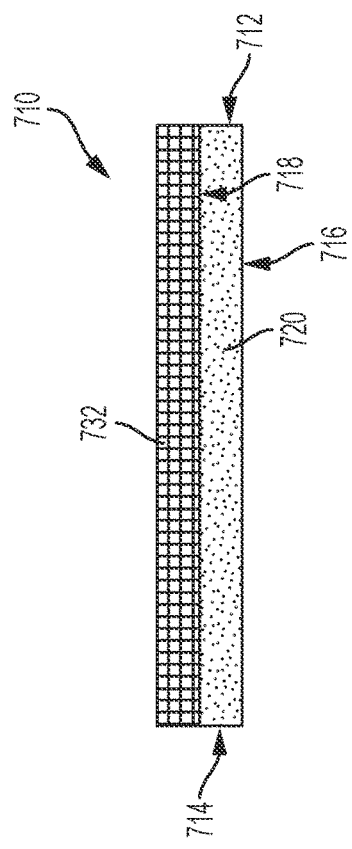
FIG. 6 is a cross section view of the leaflet shown in FIG. 4, taken along line 6-6, according to some embodiments.
Figure 7A:
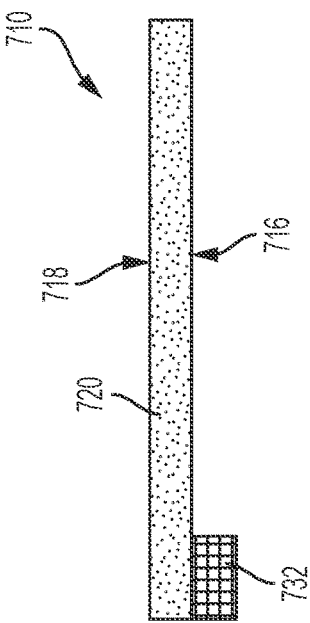
FIG. 7A is a cross section view of a leaflet, according to some embodiments.
Figure 7B:
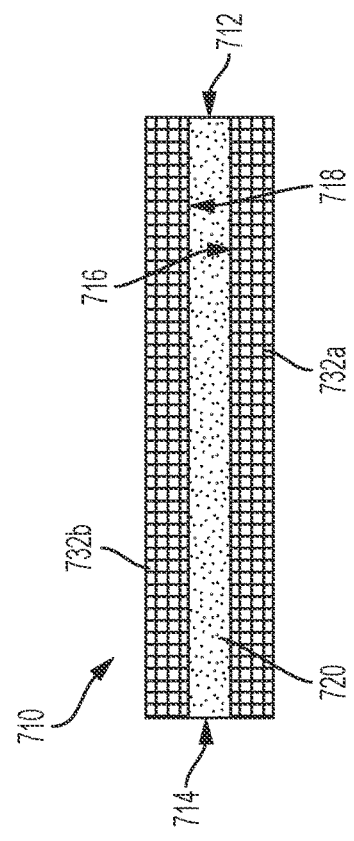
FIG. 7B is a cross section view of a leaflet, according to some embodiments.
Figure 7C:
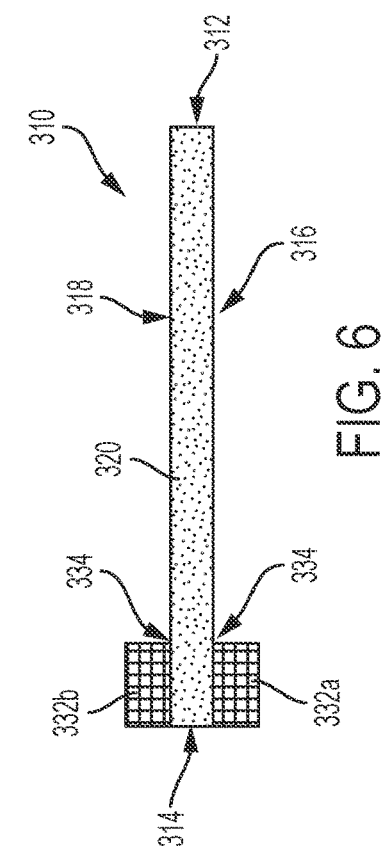
FIG. 7C is a cross section view of a leaflet, according to some embodiments.

Turning now to FIG. 6 and FIGS. 7A to 7C, in various examples, one or more synthetic tissue ingrowth curtains 332 are applied to a leaflet base 320. FIG. 6 is a cross section view of the leaflet 310. FIGS. 7A to 7C are cross section views (similar to that of FIG. 6) of the leaflet 710. FIG. 7B, for example, is a cross section view of the leaflet 710 of FIG. 9 taken along line 7B-7B. FIGS. 7A and 7C are cross section views similar to that of FIG. 7C except that the leaflets 710 shown in FIGS. 7A and 7C include alternative configurations for applying a tissue ingrowth curtain 732 to the underlying leaflet base 720.

As shown in FIGS. 4 and 6, the leaflet 310 includes a leaflet base 320 and a tissue ingrowth curtain 332. As discussed above, in various examples, the tissue ingrowth curtain 332 is applied to a portion of less than all of the leaflet base 320. For example, as shown in FIGS. 4 and 6, the tissue ingrowth curtain 332 extends from an edge 314 of the leaflet 310 opposite the leaflet free edge 312, and extends onto the leaflet belly region 322 toward the leaflet free edge 312. In various examples, the tissue ingrowth curtain 332 extends onto or across a portion of the leaflet belly region 322 and terminates thereon such that a boundary 334 is defined at an intersection between the tissue ingrowth curtain 332 and the leaflet belly region 322. As shown in FIG. 4, the boundary 334 is generally complimentary to the edge 314, however, as discussed below, other configurations are contemplated. As discussed further below with regard to FIGS. 8 to 13, the leaflet 310 can be configured with the tissue ingrowth curtain terminating in the leaflet belly region 322 such that the boundary 334 adopts virtually any linear or nonlinear, continuous, or discontinuous (e.g., multiple boundaries) profile.

Moreover, as discussed above and as shown in FIG. 6, the leaflet 310 includes a plurality of tissue ingrowth curtains, such as tissue ingrowth curtain 332a and tissue ingrowth curtain 332b. That is, the leaflet 310 is configured with tissue ingrowth curtains disposed on both an inflow side 316 and an outflow side 318 of the leaflet 310. Thus, it will be appreciated that the leaflet 310 can be constructed with a tissue ingrowth curtain 332 coupled to or otherwise disposed over one or more portions of one or both sides of the leaflet base 320. As shown, the first tissue ingrowth curtain 332a is coupled to or otherwise disposed over the inflow side 316 of the leaflet base 320 and the second tissue ingrowth curtain 332b is coupled to or otherwise disposed over the outflow side 318 of the leaflet base 320.

While the leaflet 310 is shown in FIG. 6 as including first and second tissue ingrowth curtains 332a and 332b disposed over a first side (e.g., an inflow side 316) and a second side (e.g., an outflow side 318), respectively, it should be appreciated that in various other examples, the leaflet 310 may be constructed such that a tissue ingrowth curtain is disposed on only one of the first side and second sides 316 and 318 of the leaflet base 320. For example, as shown in FIG. 7A, a leaflet 710 includes an underlying leaflet base 720 and a first tissue ingrowth curtain 732 disposed on a first side 716 of the leaflet 710 (e.g., on an inflow side of the underlying leaflet base 720). It will be appreciated that the first tissue ingrowth curtain 732 may alternatively be disposed on a second side 718 of the leaflet 710 (e.g., on an outflow side of the underlying leaflet base 720).

Additionally, as discussed above, in some embodiments, the leaflet 310 is configured such that one or more tissue ingrowth curtains 732 cover one or both sides of the underlying leaflet base 720 entirely. For example, as shown in FIGS. 7B and 9, a leaflet 710 includes an underlying leaflet base 720 and a first tissue ingrowth curtain 732 disposed on a second side 718 of the leaflet 710 such that the first tissue ingrowth curtain 732 covers the second side 718 of the leaflet 710 entirely. As discussed above, it will be appreciated that the first tissue ingrowth curtain 732 may alternatively be disposed on a first side 716 of the leaflet 710. Moreover, as discussed above, in some examples, a second tissue ingrowth curtain may be disposed on a second side 718 of the leaflet 710 in addition to any tissue ingrowth curtain disposed on the first side 716 of the leaflet 710. For example, as shown in FIG. 7C, a leaflet 710 includes an underlying leaflet base 720 and a first tissue ingrowth curtain 732a disposed on a first side 716 of the leaflet 710 (e.g., on an inflow side of the underlying leaflet base 720) such that the first tissue ingrowth curtain 732a covers the first side 716 of the leaflet 710 entirely. As shown in FIG. 7C, a second tissue ingrowth curtain 732b disposed on a second side 718 of the leaflet 710 (e.g., on an outflow side of the underlying leaflet base 720) such that the second tissue ingrowth curtain 732b covers the second side 718 of the leaflet 710 entirely.

Additionally, while the first and second tissue ingrowth curtains 332a and 332b shown in FIG. 6 are essentially mirror images of one another, the leaflet 310 may be constructed such that a first tissue ingrowth curtain disposed on a first side (e.g., an inflow side) of the leaflet base 320 has a different profile and/or cross section than does a second tissue ingrowth curtain disposed on a second side (e.g., an outflow side) of the leaflet base 320. For instance, in some examples, given the differing environmental conditions and dynamics on the inflow and outflow sides of the prosthetic valve 100, it may be desirable to configure the leaflet such that a first side of the leaflet includes a first tissue ingrowth curtain having a first size, and/or a first material, and/or a first shape, and/or a first cross section, and/or a first boundary having a first profile, and such that a second side of the leaflet includes a second tissue ingrowth curtain having a second size, and/or a second material, and/or a second shape, and/or a second cross section, and/or a second boundary having a second profile.

For example, as shown in FIGS. 8A to 8C, similar to leaflet 310, a leaflet 810 includes an underlying leaflet base 820, a leaflet free edge 812, an edge 814, first and second sides 816 and 818, a leaflet belly region 822, a leaflet base 825, and a leaflet attachment region 830. The leaflet 810 further includes a first tissue ingrowth curtain 832a disposed over a portion of the first side 816 of the leaflet 810 (e.g., on an inflow side of the underlying leaflet base 820), and a second tissue ingrowth curtain 832b disposed over the second side 818. The first tissue ingrowth curtain 832a extends onto or across a portion of the leaflet belly region 822 on the first side 816 and terminates such that a boundary 834a is defined at an intersection between the first tissue ingrowth curtain 832a and the leaflet belly region 822. The second tissue ingrowth curtain 832b extends across the leaflet belly region 822 on the second side 818 and terminates such that a boundary 834b is defined at an intersection between the second tissue ingrowth curtain 832b and the leaflet belly region 822 (which in this instance corresponds with the leaflet free edge 812). Thus, as shown, the second tissue ingrowth curtain 832b has a different cross section and/or boundary profile and/or shape and/or size than the first tissue ingrowth curtain 832a.

FIGS. 10 to 13 show a variety of additional configurations for a leaflet 310 including a tissue ingrowth curtain 332. FIG. 10 shows a leaflet 310 having a tissue ingrowth curtain 332 applied to a portion of a leaflet base 320 and terminating in the leaflet belly region 322 at approximately a midpoint between the leaflet free edge 312 and edge 314 such that the boundary 334 is substantially linear. It will be appreciated that, in some other examples, the tissue ingrowth curtain 332 may larger or smaller than that shown in FIG. 10 such that the linear boundary shown in FIG. 10 may shift closer to (or alternatively farther away from) the leaflet free edge 312.

Additionally, while the tissue ingrowth curtain may terminate into the leaflet belly such that the boundary 334 adopts a linear profile (see, e.g., FIG. 10), in some other examples, the tissue ingrowth curtain may terminate into the leaflet belly such that the boundary 334 adopts a nonlinear profile. FIGS. 11 and 12 show a leaflet 310 having a tissue ingrowth curtain 332 applied to a portion of a leaflet base 320 and terminating in the leaflet belly region 322 such that the boundary 334 adopts a nonlinear shape. As shown in FIG. 11, the boundary 334 adopts a convex shape relative to the leaflet free edge 312. As shown in FIG. 12, the boundary 334 adopts a concave shape relative to the leaflet free edge 312. In some examples, the tissue ingrowth curtain may taper where it terminates into the leaflet free edge 312. In other examples, the tissue ingrowth curtain may taper into the edge 314. In some examples, such a taper operates to minimize tissue growing between adjacently situated leaflets (e.g., bridging across adjacently situated leaflets from one tissue ingrowth curtain to another).

As mentioned above, in some examples, one or more tissue ingrowth curtains can be applied to an underlying leaflet base such that a profile of the boundary between the leaflet belly region and the tissue ingrowth curtains is discontinuous. With reference now to FIG. 13, a leaflet 310 includes a first tissue ingrowth curtain 332a applied to a first portion of a first side of a leaflet base 320 and a second tissue ingrowth curtain 332b applied to a second portion of the first side of the leaflet base 320. As shown, the leaflet 310 includes a first boundary 334a and a second boundary 334b. While the leaflet 310 shown in FIG. 13 includes two distinct tissue ingrowth curtains applied to one side of an underlying leaflet base, it will be appreciated that three or more distinct tissue ingrowth curtains may be applied to a given side of the underlying leaflet base without departing from the spirit or scope of the present disclosure. For instance, in some examples, a plurality of distinct tissue ingrowth curtains may be applied to a given side of the underlying leaflet base to achieve a designated pattern (e.g., tiled).

The tissue ingrowth curtains discussed herein may be applied, bonded, or otherwise coupled with the underlying leaflet base according to methods known to those of skill in the art. For instance, in some examples, one or more adhesives, such as FEP, may be used to bond the tissue ingrowth curtains to the underlying tissue leaflet base. Other suitable adhesive include, but are not limited to urethane, thermoplastics, fluoropolymers, silicone/urethane blends, epoxies, fluoroelastomers, FEP, and copolymers of FEP. Such adhesives may be applied to one or more of the underlying leaflet base and the tissue ingrowth curtain. In some such examples, the underlying adhesive is wicked or imbibed into the underlying leaflet base and/or the tissue ingrowth curtain prior to combining the underlying leaflet base and the tissue ingrowth curtain. In some examples, the underlying leaflet base and the tissue ingrowth curtain may additionally or alternatively be subjected to one or more thermal processes and/or pressing processes to facilitate bonding between the tissue ingrowth curtain and the underlying leaflet base.

While the above-discussed tissue ingrowth curtains generally include membranes, films, knits, or other structures that are bonded, applied, or otherwise attached to the underlying leaflet base, as mentioned above, in some examples the tissue ingrowth curtain(s) may be applied to the underlying leaflet base in the form of one or more coatings. In some such example, a coherent irregular network is distributed or deposited onto one or more portions, regions, sections, areas, or zones of the underlying leaflet base. Examples of distributing such coherent irregular networks are illustrated and described in U.S. patent application Ser. No. 12/879, 333, the contents of which are incorporated herein by reference. In some examples, the coherent irregular network is applied to one or more portions of the underlying leaflet base to create a surface texture suitable for supporting the ingrowth and proliferation of tissue, as those of skill will appreciate. For example, the coherent irregular network may be selectively applied to one or more discrete or designated sections, portions, or regions of the underlying leaflet base. In some such examples, the coherent irregular network is applied to the designated areas by masking or otherwise covering those portions of the underlying leaflet where ingrowth of tissue is undesirable such that the cover or mask can be removed subsequent to the coherent irregular network application process to achieve a leaflet having a first region including the coherent irregular network and a second region free of a coherent irregular network. In some examples, one or more sacrificial sheets, such as one or more polyimide sheets (e.g., Kapton sheets), are arranged on the underlying leaflet base and operate to mask or otherwise prevent the coherent irregular network from being applied to the masked or covered areas. Some nonlimiting examples of sacrificial sheet materials include polyester, polyetheretherketone (PEEK), PET, ePTFE/Kapton blends such as mapton, ePTFE, PTFE, silicones, and stainless steel, or other thin metal sheeting. In some examples, the one or more sacrificial sheets can be removed after the coherent irregular network application process to reveal a leaflet having a structure including one or more regions including the coherent irregular network and one or more regions free of the coherent irregular network (e.g., where the underlying leaflet base material is exposed). Such a configuration provides for a construction of the leaflet that minimizes a possibility for delamination between bonded membrane layers.

As mentioned above, in some examples, in addition to or as an alternative to applying one or more tissue ingrowth curtains to the underlying leaflet base, the underlying leaflet base materials themselves are configured to promote or accommodate tissue ingrowth. For instance, in some examples, the underlying leaflet base materials are configured such that tissue is encouraged to grow (or is not otherwise prevented or inhibited from growing) into and/or onto one or more discrete or designated sections, portions, or regions of the one or more underlying leaflet base materials. For instance, as mentioned above, the composite material forming the underlying synthetic leaflet base may include an elastomer and/or an elastomeric material such as a fluoroelastomer imbibed or otherwise incorporated into the expanded fluoropolymer membrane. In various examples, to achieve an underlying leaflet base that promotes or otherwise accommodates the ingrowth and proliferation of tissue the expanded fluoropolymer membrane is selectively imbibed, such as with one or more fluoroelastomers, such that the expanded fluoropolymer membrane includes one or more discrete portions, regions, sections, zones, or areas that are free of or are not otherwise imbibed with the elastomeric filler material (or at least are not filled to the extent that the elastomeric filler material operates to prevent tissue ingrowth). Selectively imbibing the underlying synthetic leaflet base material may be done in accordance with techniques as known to those of skill in the art.

FIGS. 14 and 15 show a leaflet 1410 having an underlying leaflet base 1420 that includes a membrane that has been selectively imbibed to form the leaflet 1410. FIG. 14 is a top view of the leaflet 1410. FIG. 15 is a cross section of the leaflet 1410 illustrated in FIG. 14 taken along line 15-15. Similar to leaflet 310, the leaflet 1410 includes an underlying leaflet base 1420, a leaflet free edge 1412, an edge 1414, first and second sides 1416 and 1418, a leaflet belly region 1422, a leaflet base 1425, and a leaflet attachment region 1430. The underlying leaflet base 1420 includes a membrane 1421. As shown, the membrane 1421 has been selectively imbibed in the belly region 1422 to form the underlying leaflet base 1420. Specifically, as shown, the portion of the membrane 1421 between the leaflet free edge 1412 and boundary 1435 has been imbibed with a filler material in accordance with the embodiments and examples discussed herein, while the portion of the membrane 1421 between the edge 1414 and the boundary 1435 remains free of any filler material. That is, the portion of the membrane 1421 between the edge 1414 and the boundary 1435 has not been imbibed. It should thus be appreciated that the boundary 1435 is defined at an intersection between the portion(s) of the membrane 1421 imbibed with a filler material and the portion(s) of the membrane 1421 that are free of filler material. Additionally, it will be appreciated that while the cross section view of FIG. 15 shows the filler material penetrating uniformly between the first and second sides 1416 and 1418 of the underlying leaflet base 1420, in some examples, the filler may penetrate only partially into the membrane 1421 beginning at each of the first and second sides 1416 and 1418. Thus, it will be appreciated that, in various examples, during the imbibing process, the filler material is imbibed into the membrane from both the first and second sides 1416 and 1418. Depending on the particular methods used, the filler material may penetrate entirely through (or alternatively partially through) the membrane 1421 between the first and second sides 1416 and 1418.

As mentioned above, the leaflet 310 may be constructed to include first and second tissue ingrowth curtains disposed on opposing first and second sides of the leaflet base 320 such that the leaflet 310 has a first tissue ingrowth curtain with a different cross section and/or boundary profile and/or shape and/or size than the second tissue ingrowth curtain. Similarly, the membrane 1421 of the leaflet 1410 may be imbibed such that the first side 1416 includes one or more portions, regions, sections, zones, or areas not imbibed with filler material (if any) that differ from the one or more portions, regions, sections, zones, or areas of the second side 1418 not imbibed with filler material (if any). In other words, the membrane 1421 of the leaflet 1410 may be imbibed such that the first side 1416 and the second side 1418 have different tissue ingrowth profiles and/or capabilities.

For example, FIG. 16 shows a cross section view of a leaflet 1410 (which is taken along a line similar to line 15-15 of FIG. 14), wherein the leaflet 1410 includes a membrane 1421 that has had a filler material imbibed across an entirety of a first side 1416 of the membrane 1421, and that has had the filler material imbibed across a portion of less than all of the second side 1418.

While the above discussed embodiments and examples include applying a tissue ingrowth curtain to one or more portions of one or more surfaces of an underlying leaflet base, or selectively imbibing one or more portions of one or more sides of a membrane of an underlying leaflet base with a filler material, it will be appreciated that, in various examples, a leaflet may be constructed by both imbibing one or more portions of the membrane and applying a tissue ingrowth curtain to the selectively imbibed underlying leaflet base. FIGS. 17 to 20 show various leaflets that include one or more selectively imbibed portions, regions, zones, or areas and that include one or more tissue ingrowth curtains.

FIG. 17 is a top view of a leaflet 1710. FIG. 18 is a cross section of the leaflet 1710 illustrated in FIG. 17 taken along line 18-18. Similar to leaflet 1410, the leaflet 1710 includes an underlying leaflet base 1720, a leaflet free edge 1712, an edge 1714, first and second sides 1716 and 1718, a leaflet belly region 1722, a leaflet base 1725, and a leaflet attachment region 1730. The underlying leaflet base 1720 includes a membrane 1721. As shown, the membrane 1721 has been selectively imbibed in the belly region 1722 to form the underlying leaflet base 1720. In particular, the membrane 1721 has been selectively imbibed in the same manner as membrane 1421 of leaflet 1410 to achieve an underlying leaflet base 1720 that is identical to the underlying leaflet base 1420. Additionally, similar to the construction of leaflet 310 shown in FIG. 4 a tissue ingrowth curtain 1732 has been applied to a portion the second side 1718 of the underlying leaflet base 1720.

In particular, the ingrowth curtain 1732 has been applied to a portion the second side 1718 of the underlying leaflet base 1720 not imbibed with the filler material (e.g., the portion of second side 1718 of the underlying leaflet base 1720 extending between the edge 1714 and the boundary 1735). Thus, the boundaries 1734 and 1735 are overlapping one another in FIG. 17. Thus, in some examples, the ingrowth curtain 1732 may be applied to an entirety of the portion the second side 1718 of the underlying leaflet base 1720 not otherwise imbibed with the filler material. Such a configuration provides that the first side 1716 of the leaflet 1710 includes a tissue ingrowth promotion region defined by a portion of the membrane 1421 not imbibed with filler material, while the second side 1718 of the leaflet 1710 includes a tissue ingrowth promotion region defined by the tissue ingrowth curtain 1732. In some examples, tissue is encouraged to grow or proliferate into and/or onto and/or across both of these tissue ingrowth regions. It will be appreciated that, in various other examples, a tissue ingrowth curtain 1732 may be additionally or alternatively applied to the portion the first side 1716 of the underlying leaflet base 1720 not imbibed with the filler material (e.g., the portion of first side 1716 of the underlying leaflet base 1720 extending between the edge 1714 and the boundary 1735).

In some examples, the ingrowth curtain 1732 may be applied to less than an entirety of those portions of the first and/or second sides 1716 and 1718 of the underlying leaflet base 1720 not otherwise imbibed, or may additionally or alternatively be applied to one or more portions of the first and/or second sides 1716 and 1718 of the underlying leaflet base 1720 imbibed with a filler material.

FIGS. 19 and 20 show a leaflet 1910 that includes one or more selectively imbibed portions, regions, zones, or areas and that includes one or more tissue ingrowth curtains. FIG. 19 is a top view of a leaflet 1910. FIG. 20 is a cross section of the leaflet 1910 illustrated in FIG. 19 taken along line 20-20.

Similar to leaflet 1710, the leaflet 1910 includes an underlying leaflet base 1920, a leaflet free edge 1912, an edge 1914, first and second sides 1916 and 1918, a leaflet belly region 1922, a leaflet base 1925, and a leaflet attachment region 1930. The underlying leaflet base 1920 includes a membrane 1921. As shown, the membrane 1921 has been selectively imbibed to form the underlying leaflet base 1920. In particular, the membrane 1921 has been selectively imbibed in the belly region 1922 in a similar manner as membrane 1721 of leaflet 1710 to achieve an underlying leaflet base 1920 that is identical to the underlying leaflet base 1720. Additionally, similar to the construction of leaflet 1710 shown in FIGS. 17 and 18, a tissue ingrowth curtain 1932 has been applied to a portion the second side 1918 of the underlying leaflet base 1920. However, as shown in FIGS. 19 and 20, the tissue ingrowth curtain 1932 extends to a position between the edge 1914 and the boundary 1935 such that a boundary 1934 is defined between the edge 1914 and the boundary 1935. That is, as shown in FIGS. 19 and 20, the tissue ingrowth curtain 1932 is applied to less than all of portion of the second side 1918 of the underlying leaflet base 1920 not imbibed with the filler material. Thus, both the tissue ingrowth curtain 1932 and a portion of the second side 1918 of the underlying leaflet base 1920 not imbibed with the filler material are exposed to surrounding tissue. In some examples, tissue may be encouraged to grow or proliferate into and/or onto and/or across both the tissue ingrowth curtain 1932 and this transition area of the underlying leaflet base 1920 between the boundaries 1934 and 1935.

It will be appreciated that, in various other examples, a tissue ingrowth curtain 1932 may be additionally or alternatively applied to a portion of less than all of the first side 1916 of the underlying leaflet base 1920 not imbibed with the filler such that a portion of the first side 1916 of the underlying leaflet base 1920 not imbibed with the filler is exposed to surrounding tissue. In some examples, tissue is encouraged to grow or proliferate into and/or onto and/or across these additional tissue ingrowth regions.

In various examples, the underlying leaflet base may be imbibed with a plurality of filler materials. That is, in some examples, a first portion, area, region, section, or zone of the membrane of underlying leaflet base may be imbibed with a first filler material while a second portion, area, region, section, or zone of the membrane of the underlying leaflet base is imbibed with a second filler material. For instance, in some examples, a first portion of the membrane of underlying leaflet base is imbibed with a first filler material such that the first portion of the membrane is resistant to or otherwise inhibits or prevents tissue ingrowth into and/or onto and/or across the first portion. However, in some examples, those portions of the membrane imbibed with the first filler may also be unsuitable for accommodating the bonding or coupling of a tissue ingrowth curtain. Accordingly, in examples where it is desirable bond or otherwise couple a tissue ingrowth leaflet to a second portion of the membrane, the second portion may be imbibed with a second filler material such that the second portion of the membrane is suited to have a tissue ingrowth curtain bonded or otherwise coupled thereto. In some examples, the second filler material may additionally or alternatively encourage tissue ingrowth. That is, in some examples, one or more portions of the membrane may be imbibed with a filler material that encourages tissue ingrowth and proliferation. Alternatively, as mentioned above, the second portion may not be imbibed with any filler material at all, but may instead remain free of filler material.

Figure 22:
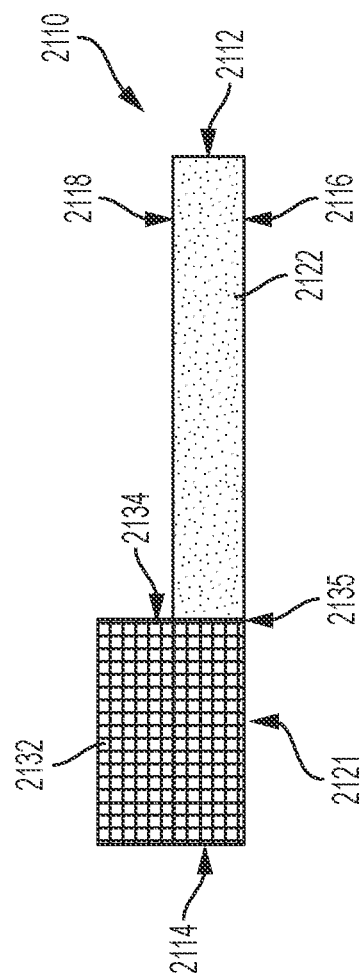
FIG. 22 is a cross section view of the leaflet shown in FIG. 21 taken along line 22-22, according to some embodiments
Figure 21:
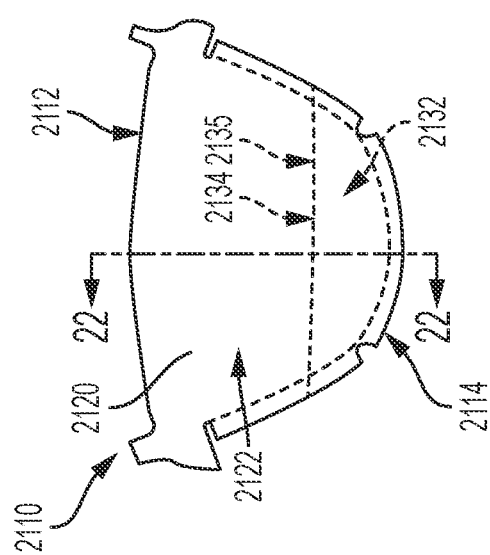
FIG. 21 is a top view of a leaflet, according to some embodiments.

FIGS. 21 and 22 show a leaflet 2110 that includes a plurality of selectively imbibed portions, regions, zones, or areas and that includes one or more tissue ingrowth curtains. FIG. 21 is a top view of a leaflet 2110. FIG. 20 is a cross section of the leaflet 2110 illustrated in FIG. 21 taken along line 20-20. As shown, the membrane includes a first portion and a second portion. The first portion of the membrane corresponds to the portion, region, zone, or area extending between the leaflet free edge 2112 and the boundary 2135, and the second portion of the membrane corresponds to the portion, region, zone, or area extending between the edge 2114 and the boundary 2135. As shown, the membrane 2121 has been selectively imbibed such that the first portion of the membrane 2121 is imbibed with a first filler material (shown as lighter shading) and such that the second portion of the membrane is imbibed with a second filler material (shown as darker shading). Additionally, as shown, a tissue ingrowth curtain 2132 has been applied to the second portion of the membrane 2121 on the second side 2118 of the underlying leaflet base 2120.

It will be appreciated that, in various examples, a tissue ingrowth curtain 2132 may be additionally or alternatively applied to the second portion of the membrane 2121 on the first side 2116 of the underlying leaflet base 2120. It will also be appreciated that the tissue ingrowth curtain 2132 may be applied to less than all of the second portion of the first and/or second sides 2116 and 2118 of the underlying leaflet base 2120. Similarly, it will be appreciated that the underlying leaflet base 2120 may be constructed such that less than all of the second portion of the membrane 2121 is imbibed with the second filler material. That is, in some examples, one or more regions or zones of the second portion may be free of both the first and the second filler material.

It has been observed that some leaflet constructions that include a tissue ingrowth curtain bonded or adhered to an underlying leaflet base have a failure mode of detachment or delamination. In some examples, detachment or delamination occurs at or near the edges of the tissue ingrowth curtain. Generally, delamination occurs between adjoining surfaces of the tissue ingrowth curtain and the underlying leaflet base proximate to or at where the adjoining surface of the tissue ingrowth curtain terminates into an edge of the tissue ingrowth curtain. Thus, in some instances, delamination or detachment occurs between adjoining surfaces of the tissue ingrowth curtain and the underlying leaflet base at or proximate where the tissue ingrowth curtain 332 and the leaflet belly region 322 intersect. Put differently, in some instances, delamination or detachment occurs at or proximate to the boundary 334, discussed above.

In some examples, to minimize a potential for delamination or detachment between the tissue ingrowth curtains and underlying leaflet bases, the adhesive or adhesive layer coupling the tissue ingrowth curtain and the underlying leaflet base together (or additionally or alternatively an additional adhesive layer) can be applied such that it forms a transition between one or more edges of the tissue ingrowth curtain and the underlying leaflet base. In some examples, such a transition area is formed across the intersection between the tissue ingrowth curtain 332 and the leaflet belly region 322 (e.g., across the boundary 334).

Turning now to FIGS. 23 and 24, a leaflet 310 includes a leaflet base 320 and a tissue ingrowth curtain 332 applied or bonded to the second side 318 of the leaflet 310 via an adhesive or adhesive layer 340. The leaflet 310 shown in FIG. 23 is similar in construction to leaflet 310 shown in FIGS. 4 and 6 with the exception that the leaflet 310 shown in FIG. 23 includes only one tissue ingrowth curtain 332, which is applied or bonded to the second side 318 of the leaflet 310. It will be appreciated that, in other examples, the leaflet includes a tissue ingrowth curtain 332 applied on both the first and second sides 316 and 318. FIG. 23 is a cross section view of a leaflet 310 that is taken along a line similar to line 6-6 in FIG. 4. As shown, the adhesive or adhesive layer 340 extends along the adjoining surfaces between the tissue ingrowth curtain 332 and the leaflet base 320. Additionally, as shown in FIG. 23, the boundary 334 marks an abrupt or sharp transition between the tissue ingrowth curtain 332 and the leaflet base 320. As mentioned above, the boundary 334 is defined along the intersection between the tissue ingrowth curtain 332, and the leaflet belly region 322 is the operating portion of the leaflet 310. Thus, those of skill in the art will appreciate that stress concentrations generally occur along the boundary 334. In some examples, these stress concentrations can be minimize by modifying the geometry of this intersection between the tissue ingrowth curtain 332 and the leaflet base 320 to more evenly distribute stress.

FIG. 24 is a cross section view of the leaflet 310 shown in FIG. 23 with the exception that the adhesive or adhesive layer 340 coupling the tissue ingrowth curtain 332 and the leaflet base 320 together is applied such that it forms a transition between one or more edges of the tissue ingrowth curtain and the underlying leaflet base. For example, as shown, the adhesive or adhesive layer 340 is applied such that a fillet 342 is formed across the transition between the tissue ingrowth curtain 332 and the leaflet base 320. In various examples, the tissue ingrowth curtain 332 and the leaflet base 320 are thermally pressed to form a natural filleted geometry. In some examples, adhesive or filler material is applied in the transition between the tissue ingrowth curtain 332 and the leaflet base 320 and utilizing one or more of heat and pressure to form the adhesive or filler material into the desired shape. In some examples, the adhesive or filler material may be in the form of a precut sheet.

A method of making a prosthetic valve in accordance with some embodiments, includes forming one or more leaflets in accordance with the above-discussed embodiments and examples, and securing the one or more leaflets to a leaflet frame. In some examples, forming the one or more leaflets includes obtaining a tube or sheet comprising one or more layers of a membrane, such as an ePTFE construct, that is suitable for forming the underlying leaflet material, as discussed herein. In some examples, one or more portions of the membrane are imbibed (entirely or selectively) with one or more filler materials such that one or more of these imbibed portions or areas are rendered unsuitable for supporting or promoting tissue ingrowth. As discussed above, the membrane may be imbibed with the filler material according to methods known to those of skill in the art.

In some examples, the method further includes providing a membrane, such as an ePTFE construct, such as a film or membrane, that is suitable for forming the tissue ingrowth curtain, as discussed herein. It will be appreciated that a variety of constructs ranging in size, shape, thickness, and material are contemplated. The method further includes bonding or otherwise coupling the tissue ingrowth curtain with the underlying leaflet base. However, in some examples, prior to applying or bonding the tissue ingrowth curtain with the underlying leaflet base, the method includes applying an adhesive to the tissue ingrowth curtain. In some examples, an adhesive, such as FEP, is wicked or imbibed into the tissue ingrowth curtain. In some examples, the adhesive is wicked or imbibed into the tissue ingrowth curtain from one or more sides of the construct. Additionally or alternatively the adhesive is wicked or imbibed into the tissue ingrowth curtain from one or more edges of the construct. In some examples, the adhesive is wicked or imbibed to a distance ranging from between five percent (5%) to ninety five percent (95%) of the thickness of the construct.

In some examples, a desired pattern for the tissue ingrowth curtain is then cut from the construct according to known methods, such as laser cutting for example. Thereafter, in some examples, the tissue ingrowth curtain is applied to the underlying leaflet base. In some examples, the tissue ingrowth curtain is layered with an accompanying underlying leaflet base and the tissue ingrowth curtain and the underlying leaflet base are bonded together. It will be appreciated that the tissue ingrowth curtain and the underlying leaflet base may be bonded according to known methods, including but not limited to, pressing, and/or thermal processing, and/or heat setting, and/or solvent welding.

In some examples, the method further includes cutting the leaflet from the resulting construct according to known methods. In some examples, a final free edge cutting operation may be performed to achieve a clean free edge of the resulting leaflet according to known methods, as those of skill will appreciate.

In some examples, the method includes applying an adhesive to the underlying leaflet base in addition to or as an alternative to applying the adhesive to the tissue ingrowth curtain, as discussed above. In some examples, an adhesive, such as FEP, is similarly wicked or imbibed into one or more portions of the underlying leaflet base, after which the tissue ingrowth curtain and the underlying leaflet base are pressed together and/or heat set according to known methods.

In some other examples, in addition to or as an alternative to applying adhesives to the tissue ingrowth curtain and the underlying leaflet base separately or individually, the tissue ingrowth curtain (e.g., having a designated pattern) and the underlying leaflet base are layered with one or more adhesives or adhesive layers therebetween, after which the layered construct is pressed and/or heat set according to known methods. The method further includes cutting the leaflet from the resulting construct according to known methods. In some examples, a final free edge cutting operation may be performed on the leaflet to achieve a clean free edge of the resulting leaflet according to known methods, as those of skill will appreciate.

In some examples, the method further includes securing the leaflets to a leaflet frame such that tissue is encouraged to grow onto and/or into the leaflets when the prosthetic valve is implanted in a patient's anatomy. In some examples, the method includes securing the leaflets to the leaflet frame such that the tissue ingrowth curtains are adjacent the leaflet frame. In some examples, the method includes securing the leaflets to the leaflet frame such that the portion of the underlying leaflet configured to promote tissue ingrowth is adjacent the leaflet frame. In some examples, the method includes securing the leaflets to the leaflet frame such that tissue is encouraged to grow across the leaflet frame and/or across the interface between the leaflets and the leaflet frame and/or onto the leaflets.

Figure 26:
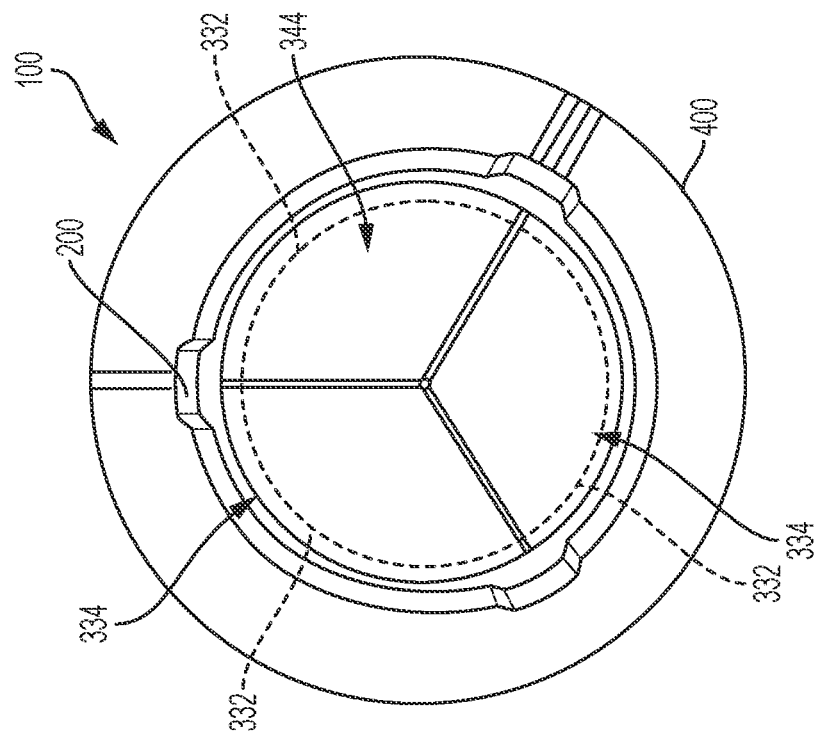
FIG. 26 is a top view of the outflow side of a prosthetic valve, according to some embodiments.
Figure 25:
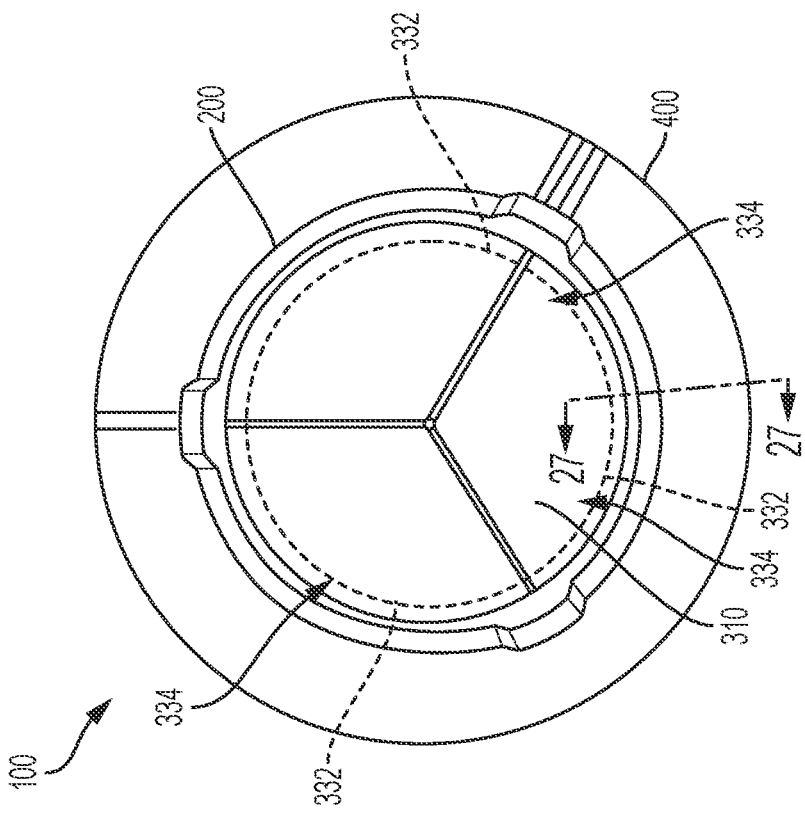
FIG. 25 is a top view of the outflow side of a prosthetic valve, according to some embodiments.
Figure 27:
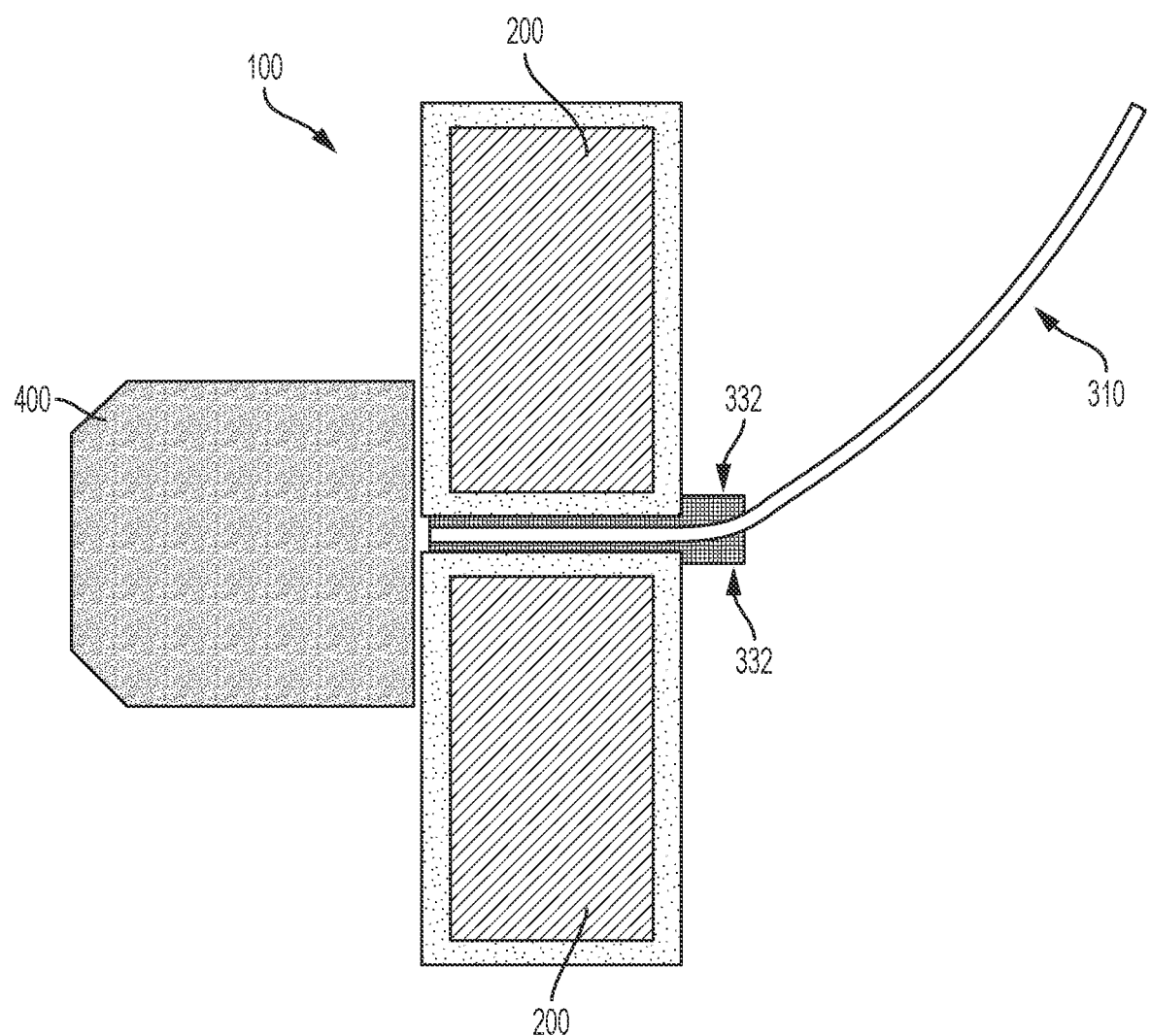
FIG. 27 is a cross section view of the prosthetic valve shown in FIG. 25 taken along line 27-27, according to some embodiments.

FIGS. 25 to 27 show an outflow side of a prosthetic valve 100 with leaflets 310 including tissue ingrowth curtains 332. FIG. 27 is a cross section view of the prosthetic valve 100 of FIG. 25 taken along line 27-27.

As shown in the FIGS. 25 and 26, the prosthetic valve 100 is constructed such that the tissue ingrowth curtain 332 of the leaflets 310 is situated adjacent the leaflet frame 200. FIG. 25 shows leaflets 310 with tissue ingrowth curtains 332 that are approximately twelve hundred microns (1.2 mm) wide, measured from the leaflet frame 200. FIG. 26 shows leaflets 310 with tissue ingrowth curtains 332 that are approximately two hundred microns (0.2 mm) wide, measured from the leaflet frame 200. The examples illustrated in FIGS. 25 and 26 should not be construed as limiting. For example, as discussed above, the tissue ingrowth curtain may be applied across an entire surface of the underlying leaflet base (see, e.g., FIGS. 7B, 7C, and 8C). While some of the above discussed embodiments and examples refer to a width of the tissue ingrowth curtain as measured from an edge 314 of the leaflet, it should be appreciated that suitable curtain widths will generally vary based on the manner in which the leaflets are attached to the leaflet frame.

Moreover, as mentioned above one or more portions of the leaflet frame 200 may be covered with material suitable for promoting tissue ingrowth. Thus, it will be appreciated that the prosthetic valve 100 is configured such that tissue is encouraged to grow onto the leaflet frame 200 (e.g., onto and/or into the material covering the leaflet frame 200), and additionally from the leaflet frame 200 onto and/or into the leaflet (e.g., the tissue ingrowth curtain and/or the portions of the underlying leaflet base configured to promote tissue ingrowth). In some examples, unlike conventional designs, the embodiments and examples discussed herein include prosthetic valve configurations including fully synthetic (or non-biological) leaflets, wherein tissue is encouraged to proliferate and grow across the interface between the leaflet frame 200 and the leaflet 310 and onto the synthetic leaflet 310. FIG. 28A is a top view of an outflow side of another prosthetic valve 100, according to some embodiments. The prosthetic valve 100 may be constructed such that a tissue ingrowth curtain 332 of leaflets 310 is situated adjacent the leaflet frame 200. The tissue ingrowth curtain 332 may be applied across an entire surface of the underlying leaflet base (see, e.g., FIGS. 7B, 7C, and 8C). While some of the above discussed embodiments and examples refer to a width of the tissue ingrowth curtain as measured from an edge of the leaflet, it should be appreciated that suitable curtain widths will generally vary based on the manner in which the leaflets are attached to the leaflet frame. In addition, the tissue ingrowth curtain 332 may be on either side (inflow and outflow) or both sides of the leaflets 310.

Moreover, as mentioned above, one or more portions of the leaflet frame 200 may be covered with material suitable for promoting tissue ingrowth. Thus, it will be appreciated that the prosthetic valve 100 is configured such that tissue is encouraged to grow onto the leaflet frame 200 (e.g., onto and/or into the material covering the leaflet frame 200), and additionally from the leaflet frame 200 onto and/or into the leaflet (e.g., the tissue ingrowth curtain and/or the portions of the underlying leaflet base configured to promote tissue ingrowth). The embodiments and examples discussed herein include prosthetic valve configurations including fully synthetic (or non-biological) leaflets, wherein tissue is encouraged to proliferate and grow across the interface between the leaflet frame 200 and the leaflet 310 and onto the synthetic leaflet 310. The prosthetic valve 100 shown in FIGS. 28-B may be a surgically implanted valve. Thus, the prosthetic valve 100 may be implanted on top of or over diseased or damaged natural leaflets of a patient. The tissue ingrowth curtain 332 may be configured to encourage tissue ingrowth from or around the natural leaflets of the patient onto the leaflet frame 200 and/or the leaflets 310.

FIG. 28B is a side view of a leaflet frame 200 of the prosthetic valve 100 shown in FIG. 28A. The leaflets 310 can be received within and coupled to the support structure 102 using any of a variety of techniques (e.g., bonding, adhering, sewing, and others). The leaflet frame 200, and thus the support structure 102 along with the leaflets 310, is optionally collapsible to a reduced profile, delivery configuration and then expandable (e.g., self-expanding or expanded by the application of an internal force, such as by balloon expansion) in situ. The leaflet frame 200 is optionally annular, defining a tapered cylinder (e.g., a cone), also described as a tapered cylindrical shape or the frame 200 may generally define a generally continuous circular transverse cross-section along the frame height in an unloaded state (e.g., when not under a transverse load). It should be understood that any variety of cross-sections (e.g., oval- or rectangular-shaped) are also contemplated.

Figure 29:
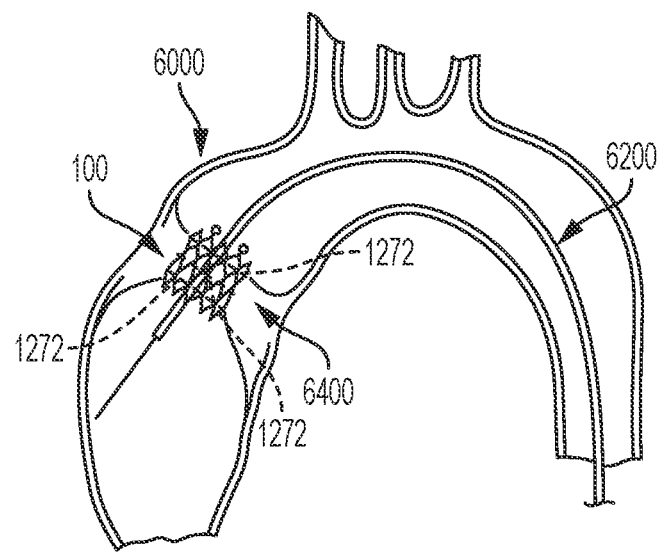
FIGS. 29 and 30 are illustrative of methods of delivering prosthetic valves to treatment locations, according to some embodiments.
Figure 30:
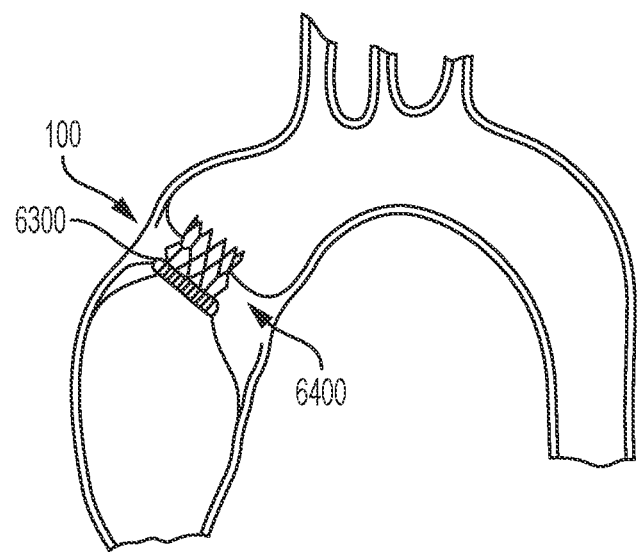

FIGS. 29 and 30 are illustrative of methods of delivering prosthetic valves to treatment locations, according to some embodiments.

Transcatheter Delivery System

In some embodiments, with reference to FIG. 29, a transcatheter delivery system 6000 comprises a prosthetic valve 6100, such as the prosthetic valve 100 shown in FIG. 28A-B, having a diametrically compacted, or collapsed configuration, and an expanded operational configuration (as shown) and a delivery catheter 6200, configured to deploy the prosthetic valve 6100. The prosthetic valve 6100 can be mounted to an end of the delivery catheter 6200 for delivery through the vasculature and maintained in a collapsed state by a plurality of constraints 1272 which are then released to permit expansion of the prosthetic valve 6100. In order to hold the prosthetic valve 6100 in a collapsed configuration on the delivery catheter 6200, the transcatheter delivery system 6000 may further comprise a removable sheath (not shown) or other type of constraint to closely fit over the prosthetic valve 100.

Some methods of delivery include the steps of radially compressing the prosthetic valve 100 into its collapsed configuration onto the end of the delivery catheter 6200; delivering the prosthetic valve 100 to a desired treatment location, including a tissue orifice 6400, such as a native valve orifice (e.g., aortic valve orifice or a mitral valve orifice), via a transfemoral or transapical route, and expanding the prosthetic valve 100 into the tissue orifice 6400. The prosthetic valve 100 can be self-expanding and/or expansion can also be facilitated by expanding a balloon (not shown).

Surgical Embodiments

It is appreciated that the prosthetic valve 100 (according to any of the examples previously described) may be surgically implanted rather than using transcatheter techniques. As shown in FIG. 30, the prosthetic valve 100 (according to any of the examples previously described) may have a sewing cuff 6300 adjacent to the frame outer side. The sewing cuff 6300, which may be of a type known in the art, is operable to provide structure that receives suture for coupling the prosthetic valve 100 to an implant site, such as the tissue orifice 6400. The sewing cuff may comprise any suitable material, such as, but not limited to, double velour polyester. The sewing 6300 cuff may be located circumferentially around the frame of the prosthetic valve 100, for example.

It should be appreciated that where the leaflet is additionally or alternatively constructed with selective imbibing in accordance with the embodiments and examples discussed above, the corresponding portions, section, regions, areas, and/or zones suitable for supporting and/or promoting tissue ingrowth may be similarly sized to the tissue ingrowth curtains.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A tissue ingrowth composite material for implantable heart valves, the tissue ingrowth composite material comprising:
   a base layer including an expanded fluoropolymer membrane having a plurality of spaces formed within a matrix of fibrils;
   a fluoroelastomer imbibed into a portion of the expanded fluoropolymer membrane without inhibiting tissue ingrowth into the portion of the expanded fluoropolymer membrane, the fluoroelastomer including tetrafluoroethylene and perfluoromethyl vinyl ether (TFE/PMVE copolymer), the TFE/PMVE copolymer comprising from 67 to 61 weight percent tetrafluoroethylene and from 33 to 39 weight percent perfluoromethyl vinyl ether; and
   a filler material imbibed into another portion of the expanded fluoropolymer membrane to inhibit tissue ingrowth into the other portion of the expanded fluoropolymer membrane.

2. The tissue ingrowth composite material of claim 1, further comprising a layer of TFE-PMVE copolymer comprising from about 73 to about 68 weight percent tetrafluoroethylene and from about 27 to about 32 weight percent perfluoromethyl vinyl ether.

3. A tissue ingrowth composite material for implantable heart valves, the tissue ingrowth material comprising:
   a base layer including an expanded fluoropolymer membrane having a plurality of spaces formed within a matrix of fibrils;
   a fluoroelastomer imbibed into a portion of the expanded fluoropolymer membrane without inhibiting tissue ingrowth into the portion of the expanded fluoropolymer membrane;
   a filler material imbibed into another portion of the expanded fluoropolymer membrane to inhibit tissue ingrowth into the other portion of the expanded fluoropolymer membrane; and
   a layer of tetrafluoroethylene and perfluoromethyl vinyl ether (TFE/PMVE copolymer) comprising from about 73 to about 68 weight percent tetrafluoroethylene and from about 27 to about 32 weight percent perfluoromethyl vinyl ether.

4. The tissue ingrowth composite material of claim 3, wherein the fluoroelastomer includes tetrafluoroethylene and perfluoromethyl vinyl ether (TFE/PMVE copolymer), the TFE/PMVE copolymer comprising from 60 to 20 weight percent tetrafluoroethylene and from 40 to 80 weight percent perfluoromethyl vinyl ether.

5. An implantable heart valve comprising:
   a frame;
   a first fluoropolymer membrane coupled to the frame, and an elastomer imbibed into a portion of the first fluoropolymer membrane without inhibiting tissue ingrowth into the portion of the first fluoropolymer membrane, and a filler material imbibed into another portion of the first fluoropolymer membrane to inhibit tissue ingrowth into the other portion of the first fluoropolymer membrane, and
   a porous tissue ingrowth curtain configured to promote tissue ingrowth coupled to at least a portion of a first side the first fluoropolymer membrane.

6. The implantable device of claim 5, wherein the porous tissue ingrowth curtain comprises a second fluoropolymer membrane.

7. The implantable device of claim 6, wherein the second fluoropolymer membrane includes an expanded fluoropolymer.

8. The implantable device of claim 7, wherein the expanded fluoropolymer membrane comprises ePTFE.

9. The implantable device of claim 5, wherein the porous tissue ingrowth curtain is coupled to the first fluoropolymer membrane with an adhesive.

10. The implantable device of claim 5, wherein the first fluoropolymer membrane includes a first zone and a second zone, the porous tissue ingrowth curtain being coupled to the second zone of the first fluoropolymer membrane.

11. The implantable device of claim 10, wherein the porous tissue ingrowth curtain is coupled to the second zone of the first fluoropolymer membrane with an adhesive.

12. The implantable device of claim 5, wherein the first fluoropolymer membrane includes a first zone, a second zone, the first side, and a second opposing side, and wherein the porous tissue ingrowth curtain completely covers the second zone of the first fluoropolymer membrane on the first side of the first fluoropolymer membrane.

13. The implantable device of claim 5, wherein the elastomer includes a fluoroelastomer.

14. The implantable device of claim 5, wherein the elastomer includes a TFE/PMVE copolymer.

\* \* \* \* \*